(12) United States Patent
Kats

(10) Patent No.: US 8,905,757 B2
(45) Date of Patent: Dec. 9, 2014

(54) METHOD AND APPARATUS FOR MEASURING A LOCATION AND ORIENTATION OF A PLURALITY OF IMPLANTS

(71) Applicant: E.Kats Enterprises Ltd., Thornhill (CA)

(72) Inventor: Eduard Kats, Thornhill (CA)

(73) Assignee: E. Kats Enterprises Ltd., Thornhill (CA)

( * ) Notice: Subject to any disclaimer, the term of this patent is extended or adjusted under 35 U.S.C. 154(b) by 0 days.

(21) Appl. No.: 13/692,262

(22) Filed: Dec. 3, 2012

(65) Prior Publication Data

US 2014/0154638 A1    Jun. 5, 2014

(51) Int. Cl.
    *A61C 19/04*     (2006.01)
    *A61C 8/00*     (2006.01)
    *A61C 9/00*     (2006.01)
    *A61C 13/34*     (2006.01)

(52) U.S. Cl.
    CPC ............. *A61C 8/0001* (2013.01); *A61C 9/0006* (2013.01); *A61C 19/04* (2013.01); *A61C 8/0048* (2013.01); *A61C 13/34* (2013.01)
    USPC .......................................................... 433/74

(58) Field of Classification Search
    USPC .......................................... 433/72, 74, 75, 76
    See application file for complete search history.

(56) References Cited

U.S. PATENT DOCUMENTS

| | | | | |
|---|---|---|---|---|
| 655,933 | A | * | 8/1900 | Le Cron .......................... 33/514 |
| 1,082,052 | A | * | 12/1913 | Strang ............................. 33/513 |
| 1,216,596 | A | * | 2/1917 | Nishi .............................. 433/75 |
| 2,644,231 | A | | 7/1953 | Brennan |
| 3,277,576 | A | * | 10/1966 | Kraft ............................... 433/53 |
| 4,234,306 | A | | 11/1980 | Hamada et al. |
| 4,575,805 | A | | 3/1986 | Moermann et al. |
| 4,657,510 | A | | 4/1987 | Gittleman |
| 4,663,720 | A | | 5/1987 | Duret et al. |

(Continued)

FOREIGN PATENT DOCUMENTS

| | | |
|---|---|---|
| BR | 0903606 | 5/2011 |
| CA | 2702273 | 4/2009 |

(Continued)

OTHER PUBLICATIONS

Osseonews.Com, Major Paradigm Shift in the Dental Implant Market, Online article: "http://www.osseonews.com/major-paradigm-shift-in-the-dental-implant-market/", May 6, 2006 [retrieved: Apr. 8, 2013].

(Continued)

*Primary Examiner* — Ralph Lewis
(74) *Attorney, Agent, or Firm* — Bereskin & Parr LLP/S.E.N.C.R.L., s.r.l.

(57) ABSTRACT

An apparatus is provided for measuring a location and orientation of each of a plurality of dental implants. The apparatus may include a base, and a plurality of extension members protruding from the base. Each of the plurality of extension members may be movable in relation to the base. Each extension member may include a proximal end connected to the base, a distal end, and a coping connected to the distal end. The coping may be movable in relation to a corresponding extension member. Furthermore, the coping may be adapted to be mechanically locked in a selected location and orientation.

18 Claims, 28 Drawing Sheets

(56) References Cited

U.S. PATENT DOCUMENTS

| | | | |
|---|---|---|---|
| 4,837,732 | A | 6/1989 | Brandestini et al. |
| 5,055,047 | A | 10/1991 | Names |
| 5,195,891 | A | 3/1993 | Sulc |
| 5,215,460 | A * | 6/1993 | Perry ............................ 433/75 |
| 5,401,170 | A | 3/1995 | Nonomura |
| 5,857,853 | A | 1/1999 | van Nifterick et al. |
| 5,870,191 | A | 2/1999 | Shirley et al. |
| 5,924,862 | A * | 7/1999 | White ............................ 433/72 |
| 5,997,299 | A * | 12/1999 | Unger ............................ 433/173 |
| 6,050,821 | A | 4/2000 | Klaassen |
| 6,056,547 | A | 5/2000 | Names |
| 6,468,078 | B2 | 10/2002 | Guillaume et al. |
| 6,692,254 | B1 | 2/2004 | Kligerman et al. |
| 6,788,986 | B1 | 9/2004 | Traber et al. |
| 6,887,078 | B2 | 5/2005 | Perot |
| 6,902,401 | B2 | 6/2005 | Jornéus et al. |
| 6,905,336 | B2 | 6/2005 | Summers |
| 7,153,135 | B1 | 12/2006 | Thomas |
| 7,214,063 | B2 | 5/2007 | Cohen |
| 7,632,096 | B2 | 12/2009 | Gittleman |
| 7,702,492 | B2 | 4/2010 | Marshall |
| 7,731,497 | B2 | 6/2010 | De Moyer |
| 7,758,346 | B1 | 7/2010 | Letcher |
| 7,806,691 | B2 | 10/2010 | Berger |
| 7,887,327 | B2 | 2/2011 | Marotta |
| 7,916,911 | B2 | 3/2011 | Kaza et al. |
| 7,922,490 | B2 | 4/2011 | Wen |
| 7,986,415 | B2 | 7/2011 | Thiel et al. |
| 8,275,184 | B2 | 9/2012 | Schneider et al. |
| 2003/0108845 | A1 | 6/2003 | Giovannone et al. |
| 2004/0155975 | A1 | 8/2004 | Hart |
| 2006/0019219 | A1 | 1/2006 | Saliger et al. |
| 2006/0024644 | A1 | 2/2006 | Cohen |
| 2007/0047079 | A1 | 3/2007 | Trissel |
| 2007/0077535 | A1 | 4/2007 | Wichmann et al. |
| 2007/0109559 | A1 | 5/2007 | Babayoff |
| 2007/0296959 | A1 | 12/2007 | Schwotzer |
| 2008/0050700 | A1 | 2/2008 | Weber et al. |
| 2008/0176188 | A1 | 7/2008 | Holzner et al. |
| 2008/0273773 | A1 | 11/2008 | Ernst |
| 2008/0286714 | A1 | 11/2008 | Haselhuhn et al. |
| 2009/0104585 | A1 | 4/2009 | Diangelo et al. |
| 2009/0133260 | A1 | 5/2009 | Durbin |
| 2009/0325127 | A1 | 12/2009 | Kusch et al. |
| 2010/0026963 | A1 | 2/2010 | Faulstich |
| 2010/0062396 | A1 | 3/2010 | Hock et al. |
| 2010/0085636 | A1 | 4/2010 | Berner |
| 2010/0208275 | A1 | 8/2010 | Babayoff |
| 2010/0209874 | A1 | 8/2010 | Auderset et al. |
| 2011/0136077 | A1 | 6/2011 | De Moyer |
| 2011/0242281 | A1 | 10/2011 | Schmidt |
| 2011/0269105 | A1 | 11/2011 | Jahn |
| 2011/0287385 | A1 | 11/2011 | Artal Arruga |
| 2012/0064477 | A1 | 3/2012 | Schmitt |
| 2012/0189985 | A1 | 7/2012 | Iglesias |
| 2012/0264082 | A1 | 10/2012 | Segura et al. |

FOREIGN PATENT DOCUMENTS

| | | |
|---|---|---|
| EP | 501940 | 2/1992 |
| EP | 599578 | 6/1994 |
| EP | 998241 | 2/1999 |
| EP | 1096897 | 1/2000 |
| EP | 1448113 | 5/2003 |
| EP | 1500380 | 5/2004 |
| EP | 1555953 | 5/2004 |
| EP | 1532938 | 9/2004 |
| EP | 1622537 | 11/2004 |
| EP | 1694235 | 6/2005 |
| EP | 1595523 | 11/2005 |
| EP | 1809198 | 12/2005 |
| EP | 1621156 | 2/2006 |
| EP | 1802249 | 4/2006 |
| EP | 1848365 | 8/2006 |
| EP | 1906862 | 1/2007 |
| EP | 1956998 | 5/2007 |
| EP | 2056735 | 11/2007 |
| EP | 1920730 | 5/2008 |
| EP | 2162700 | 5/2008 |
| EP | 1961397 | 8/2008 |
| EP | 1970025 | 9/2008 |
| EP | 1985256 | 10/2008 |
| EP | 2185095 | 3/2009 |
| EP | 2211757 | 4/2009 |
| EP | 2113222 | 11/2009 |
| EP | 2130514 | 12/2009 |
| EP | 2335639 | 12/2009 |
| EP | 2204138 | 7/2010 |
| EP | 2393446 | 8/2010 |
| EP | 2266494 | 12/2010 |
| EP | 2319451 | 5/2011 |
| EP | 2322115 | 5/2011 |
| EP | 2335640 | 6/2011 |
| EP | 2345386 | 7/2011 |
| EP | 2366359 | 9/2011 |
| EP | 2218423 | 5/2012 |
| WO | 9634576 | 11/1996 |
| WO | 9904723 | 2/1999 |
| WO | 0002497 | 1/2000 |
| WO | 0182818 | 11/2001 |
| WO | 0185048 | 11/2001 |
| WO | 0197706 | 12/2001 |
| WO | 0226157 | 4/2002 |
| WO | 03037208 | 5/2003 |
| WO | 2010021535 | 5/2003 |
| WO | 2004017858 | 3/2004 |
| WO | 2004039280 | 5/2004 |
| WO | 2004100822 | 5/2004 |
| WO | 2004066861 | 8/2004 |
| WO | 2004108014 | 12/2004 |
| WO | 2005004739 | 1/2005 |
| WO | 2005055856 | 6/2005 |
| WO | 2005084576 | 9/2005 |
| WO | 2005120383 | 12/2005 |
| WO | 2006038877 | 4/2006 |
| WO | 2006079188 | 8/2006 |
| WO | 2006103648 | 10/2006 |
| WO | 2006108370 | 10/2006 |
| WO | 2007005490 | 1/2007 |
| WO | 2007050436 | 5/2007 |
| WO | 2007061382 | 5/2007 |
| WO | 2007128263 | 11/2007 |
| WO | 2008005432 | 1/2008 |
| WO | 2008050373 | 5/2008 |
| WO | 2008051129 | 5/2008 |
| WO | 2008051142 | 5/2008 |
| WO | 2008062418 | 5/2008 |
| WO | 2008145687 | 5/2008 |
| WO | 2008077443 | 7/2008 |
| WO | 2009055211 | 4/2009 |
| WO | 2009058656 | 5/2009 |
| WO | 2009068559 | 6/2009 |
| WO | 2009115283 | 9/2009 |
| WO | 2009120312 | 10/2009 |
| WO | 2009146195 | 12/2009 |
| WO | 2010048558 | 4/2010 |
| WO | 2010083393 | 7/2010 |
| WO | 2010089698 | 8/2010 |
| WO | 2010091868 | 8/2010 |
| WO | 2010093737 | 8/2010 |
| WO | 2010097214 | 9/2010 |
| WO | 2010145669 | 12/2010 |
| WO | 2011030342 | 3/2011 |
| WO | 2011050425 | 5/2011 |
| WO | 2011078617 | 6/2011 |

OTHER PUBLICATIONS

PRnewswire.Com, Indian Market for Dental Imaging Equipment 2011 (Digital Intraoral X-Ray Systems, Extraoral X-Ray Systems and CBCT Scanners), Online article: "http://www.prnewswire.com/news-releases/indian-market-for-dental-imaging-equipment-2011-

(56) References Cited

OTHER PUBLICATIONS digital-intraoral-x-ray-systems-extraoral-x-ray-systems-and-cbct-scanners-124960014.html", Apr. 7, 2011 [retrieved: Apr. 8, 2013].
Worldwide Nanotechnology Dental Implant Market Shares, Strategies, and Forecasts, 2009 to 2015-Aarkstore Enterprise "http://www.thelostring.com/2010/09/14/worldwide-nanotechnology-dental-implant-market-shares-strategies-and-forecasts-2009-to-2015-aarkstore-enterprise" Sep. 14, 2010 [retrieved: Jun. 15, 2013].
AFG Research, Market Research Report—Dental Industry—4th Quarter 2010 U.S. Market Snapshot Series Report for CBCT and Digital Panoramic X-Ray, Online report summary: "http://www.afg-research.com/report/dental/100233-651.htm", Oct. 13, 2010 [retrieved: Jun. 15, 2013].
The Tooth Studio, All on 4, All on 5, All on 6, Online article: "http://toothstudio.com/all-on-4.php", undated [retrieved: Apr. 8, 2013].
Dentalaegis.Com, Image Guidance for Implants Improves Accuracy and Predictability, Online report: "http://www.dentalaegis.com/special-issues/2011/12/image-guidance-for-implants-improves-accuracy-predictability", Nov./Dec. 2011—vol. 32, Issue 4 [retrieved: Apr. 8, 2013].
Cone Beam Computed Tomography (CBCT), "http://sidekickmag.com/technology/articles/cone-beam-ct-technology-clinical-benefits-in-today%E2%80%99s-dental-practice_395.html", Jan. 23, 2012, [retrieved: Jun. 15, 2013].
The Endo Blog, Explanation of Cone Beam Computed Tomography (CBCT), Online article: "http://www.theendoblog.com/2011/02/cone-beam-computed-tomography-cbct.html", Feb. 18, 2011 [retrieved: Apr. 8, 2013].
Allon4implants.Com, All-On-4 Implants Canada, Online article: "http://www.allon4dentalimplants.com/", undated [retrieved: Apr. 8, 2013].
Tekscan, Pressure and Force Measurement Applications, Webpage: "http://www.tekscan.com/applications" undated [retrieved: Apr. 8, 2013].
SCDlab.Com, Features & Benefits, Webpage: "http://www.scdlab.com/godigital/intra-oral-scanners/CEREC-Connect/cerec-features-benefits", undated [retrieved: Apr. 8, 2013].
Ruth Iverson, CAD/CAM and wax printers, Online discussion: "http://www.webdental.com/group/digitalimaging/forum/topics/cadcam-and-wax-printers?xg_source=activity", Feb. 28, 2010 [retrieved: Apr. 8, 2013].
Doctorbicuspid.Com (Laird Harrison), Digital impressions competition booming, Online article: "http://www.drbicuspid.com/index.aspx?sec=sup&sub=rst&pag=dis&ItemID=301650", Mar. 31, 2009 [retrieved: Apr. 8, 2013].
Birnbaum NS, Aaronson HB, Stevens C, Cohen B: 3D Digital Scanners: A High-Tech Approach to More Accurate Dental Impressions, Inside Dentistry; 2009; 5: 70-74.
Sirona.Com, CEREC Chairside Solutions, Online article: "http://www.sirona.com/ecomaXL/index.php?site=SIRONA_COM_cerec_nl_2009-01", undated [retrieved: Apr. 8, 2013].
Dentalblogs.Com, Sirona Introduces CEREC® AC Powered by Bluecam, Online article: "http://www.dentalblogs.com/archives/administrator-2/sirona-introduces-cerec%C2%AE-ac-powered-by-bluecam/", Jan. 7, 2009 [retrieved: Apr. 8, 2013].
Forb.It, Attrezzature, Prodotti e Novità, Webpage: "http://www.forb.it/viewdoc.asp?co_id=29", undated [retrieved: Apr. 8, 2013].
Cerecwerx, Photo Gallery, Webpage: "http://www.cerecwerx.com/cerec_photos.html", undated [retrieved: Apr. 8, 2013].
3M, 3M ESPE Dental Supplies, Webpage: "http://solutions.3m.co.za/wps/portal/3M/en_ZA/3M-ESPE/dental-professionals/solutions/dental-lab/lava-cos/", undated [retrieved: Apr. 8, 2013].
Benco Dental, Making the Switch to the Lava C.O.S, Online article: "http://www.benco.com/About/News/ Making_the_Switch_to_the_Lava_C_O_S_.aspx", Apr. 5, 2010, [retrieved: Apr. 8, 2013].
PRWEB.Com, IOS Technologies and Glidewell Laboratories Announce Beta Testing of IOS FastScan(TM) Intraoral Digital Scanner, Online article: "http://www.prweb.com/releases/glidewell-dental-lab/ios-fastscan/prweb4313694.htm", Jul. 28, 2010 [retrieved: Apr. 8, 2013].
Michael C. Ditolla, Clinical Tips, Online article: "http://mobile.glidewelldental.com/mobile/dentist/chairside-magazine/2011-v6-1/featured-articles/dr-d-clinical-tips.aspx", undated [retrieved: Apr. 8, 2013].
Dphotonics.Com, Technology, Webpage: "http://www.dphotonics.com/technology", undated [retrieved: Apr. 8, 2013].
DDN-Online.Net, Intraoralscanner Hint-ELs® directScan, Webpage: "http://www.ddn-online.net/info/index.php?cat=5&id=88", Jan. 22, 2009 [retrieved: Apr. 8, 2013].
Science Illustrated, New scanner takes 3D photos of your teeth, Online article: "http://scienceillustrated.com.au/blog/medicine/new-scanner-takes-3d-photos-of-your-teeth/", Oct. 7, 2010 [retrieved: Apr. 8, 2013].
Direct Metal Laser Sintering, Additive Manufacturing of DMLS Parts, Online article: "http:// directmetallasersintering.blogspot.com/", May 31, 2012[retrieved: Apr. 8, 2013].
GPI Prototype & Manufacturing Services, Direct Metal Laser Sintering (DMLS), Online article: "http:// gpiprototype.com/services/dmls-direct-metal-laser-sintering.html", undated [retrieved: Apr. 8, 2013].
Keiji Iwasaki, Shoji Ohkawa, Motohiro Uo, Tsukasa Akasaka, Fumio Watari, Laser Welding of Titanium and Dental Precious Alloys, Materials Transactions, vol. 45, No. 4 (2004) pp. 1140 to 1146.
Roy Raviv, Implant Supported-Titanium Milled Bar Over-Dentures: Clinical Case Report, Online article: "http://www.oralhealthgroup.com/news/implant-supported-titanium-milled-bar-over-dentures-clinical-case-report/1000535341/" Jan. 8, 2011[retrieved: Apr. 8, 2013].
Andrew Wilson, 3-D Scanner Images Dental Molds, Online article: "http://www.vision-systems.com/articles/print/volume-17/issue-6/features/3-d-scanner-images-dental-molds.html", Jun. 1, 2012[retrieved: Apr. 8, 2013].
Statistics Canada, Projected population by age group and sex according to three projection scenarios for 2010, 2011, 2016, 2021, 2026, 2031 and 2036, at Jul. 1, Online report: "http://www.statcan.gc.ca/tables-tableaux/sum-som/I01/cst01/demo23c-eng.htm", Nov. 16, 2010[retrieved: Apr. 8, 2013].
Free Press Release, Dental Implant Market is Growing Globally, Online article: "http://www.free-press-release.com/news-dental-implant-market-is-growing-globally-1284004777.html", Sep. 8, 2010[retrieved: Apr. 8, 2013].
Nicola D'Apuzzo, Human Body Measurement Newsletter, vol. 4, No. 1, Aug. 2009.
Youtube, All on 4 technique, Online video: "http://www.youtube.com/watch?v=-WNvhVR35KA", Sep. 8, 2012[retrieved: Apr. 11, 2013].
Youtube, Osseolink Maxillary Implants—Part 6 (impression 1 of 2), Online video: "http://www.youtube.com/watch?v=9gkOFWXrY-s&feature=related", Dec. 29, 2010[retrieved: Apr. 11, 2013].
Youtube, Osseolink Maxillary Implants—Part 7 (Impression 2 of 2), Online video: "http://www.youtube.com/watch?v=d5UGAael_RQ", Dec. 31, 2010[retrieved: Apr. 11, 2013].
Youtube, Osseolink Maxillary Implants—Part 8 (Restorations), Online video: "http://www.youtube.com/watch?v=Mr9HjDZtJ2c", Feb. 1, 2011[retrieved: Apr. 11, 2013].
Youtube, Procedure All on 4 step by step (photo slideshow), Online video: "http://www.youtube.com/watch?v=HT1eigG3SRQ&feature=related", Jan. 19, 2011[retrieved: Apr. 11, 2013].
Youtube, Dental Implant Digital Impression CAD/CAM restoration by PlCdental & exocad (wax-up reduction), Online video: "http://www.youtube.com/watch?v=SoFjpmuY1jw&feature=relmfu", Feb. 1, 2012[retrieved: Apr. 11, 2013].
Youtube, See how to make a Digital Impression with Lava COS, Online video: "http://www.youtube.com/watch?v=SDHStihaLuE&feature=related", Oct. 20, 2010[retrieved: Apr. 11, 2013].
Youtube, 3Shape TRIOS—intraoral scanner, Online video: "http://www.youtube.com/watch?v=KKdxynvRbSY&feature=related", May 29, 2011[retrieved: Apr. 11, 2013].
Youtube, Protocolo sobre implantes, Online video: "http://www.youtube.com/watch?v=u_NRCuAKkDI&feature=related", Aug. 12, 2010[retrieved: Apr. 11, 2013].

\* cited by examiner

METHOD AND APPARATUS FOR MEASURING A LOCATION AND ORIENTATION OF A PLURALITY OF IMPLANTS

FIELD

This application relates to the field of dental implant systems.

INTRODUCTION

Dental implants, anchored into a patient's jaw, may be used to permanently affix a dental prosthesis into a patient's mouth. The dental prosthesis will typically include one or more artificial teeth. In many cases, a dental prosthesis is configured to mount onto an underlying framework, which may be made of titanium or another suitable material. The framework is secured to the dental implants using fasteners such as screws, for example.

It is desirable for the location and orientation of implant interfaces in a dental framework to be precisely aligned with the implants in a patient's mouth. The position of each implant may vary by up to six degrees of freedom (e.g. location along and orientation about x, y and z axes). Misalignment of an implant interface may cause stress upon the framework or the jaw bone after the fasteners are tightened. This may result in a cracked dental prosthesis and compromised implants. Accordingly, there is a benefit to accurately determining the location and orientation of each dental implant that will support a dental framework.

One method for measuring the location and orientation of dental implants is cone beam computed tomography (CBCT). In this method, a series of x-ray scans are taken about the head of a patient, and interpolated using software to generate a 3D model. However, the accuracy of measurements taken using CBCT is limited by the positional accuracy of the mechanical system, the cone beam projector geometry, the sensitivity of the detector, the contrast resolution, and a patient's natural movements (e.g. breathing).

Another method for measuring the location and orientation of dental implants uses three-dimensional (3D) intraoral scanners. These methods typically involve capturing images of a patient's mouth from multiple angles, and processing the images using computer software to generate a 3D model. The accuracy of this method is limited by the positions of the scanner relative to measured objects, the type and quality of dental coatings used, the natural shaking of an orthodontist's hand, and a patient's natural movements (e.g. breathing).

Another method for measuring the location and orientation of dental implants is to take an impression manually. This method typically begins with applying impression material inside a patient's mouth (e.g. using an impression tray). The impression material sets as an elastic solid, and when removed from the patient's mouth provides a negative model of the patient's dentition. Casting material may then be applied to the negative model to produce a positive model that may be scanned using a computer to generate a 3D model. The accuracy of this method is limited by the low rigidity and non-uniform shrinkage of the impression material during curing, both of which may cause the dental implant impressions to shift position.

Another method for measuring the location and orientation of dental implants uses telescoping crossbrace members connected in series from one implant to the next. Each end of each crossbrace member has an implant screw for securing to a patient's implant. Each screw has angular freedom to rotate and align with the implant. In use, the screws are secured to a patient's implants, then adhesive is applied to inhibit any further telescoping or rotating of the crossbrace members or the screws. An impression tray filled with impression material may then be applied over the crossbrace members and gum tissue. Then the screws are withdrawn from the implants and the apparatus including the impression tray and impression material is removed from the patient's mouth. The accuracy of this method is limited by the capacity of the adhesive to prevent the crossbrace members and the screws from moving or rotating when applying the impression material and during the curing process.

SUMMARY

In accordance with at least one embodiment, an apparatus is provided for measuring a location and orientation of each of a plurality of dental implants. The apparatus may include a base, and a plurality of extension members protruding from the base. Each of the plurality of extension members may be movable in relation to the base. Each extension member may include a proximal end connected to the base, a distal end, and a coping connected to the distal end. The coping may be movable in relation to a corresponding extension member. Furthermore, the coping may be adapted to be mechanically locked in a selected location and orientation.

The apparatus may also include a plurality of clamps. Each of the plurality of clamps may be adapted to lock a corresponding extension member to the base. Also, each of the plurality of clamps may be adapted to lock a corresponding coping in a selected location and orientation. Each extension member may comprise an elongate upper portion and an elongate lower portion and each of the plurality of clamps may be adapted to urge one of the upper and lower portions toward the other of the upper and lower portions of a corresponding extension member.

Each coping may be at least partially received in a corresponding spherical member. Also, each of the plurality of clamps may be adapted to urge the upper and lower portions of the corresponding extension member against an external surface of the corresponding spherical member to lock a location and orientation of the corresponding spherical member with respect to the extension member.

Each coping may be at least partially received in a through-hole of the corresponding spherical member. The through-hole may be defined by an interior surface of the spherical member. Each of the plurality of clamps may be adapted to urge the upper and lower portions of the corresponding extension member against the external surface of the corresponding spherical member to reduce a diameter of the through-hole of the corresponding spherical member thereby urging the interior surface of the corresponding spherical member against the corresponding coping. This may lock the location and orientation of the coping with respect to the base.

The coping may be connected to the corresponding extension member by a ball joint.

In at least one embodiment, the base may include at least one slot. Also, each of the plurality of clamps may pass through one of the at least one slot, and each of the plurality of clamps may be adapted to lock the corresponding extension member relative to the corresponding slot.

Each coping may define a through-hole that is adapted to receive a screw connected to one of the plurality of dental implants. Also, the through-hole of each coping may be sized to receive a measurement target detectable by a control measurement device.

A location and orientation of each coping may be fixed with respect to the corresponding extension member. However, each coping may be rotatable about the corresponding extension member in at least two orthogonal axes. Also, each clamp may be adapted to resist rotation of the corresponding coping relative to the corresponding extension member.

At least one extension member may be translatable along a plane, and each extension member may be rotatable about an axis perpendicular to the plane. The axis may be concentric with the corresponding clamp.

In accordance with at least one embodiment, a method is provided for making a dental framework for a plurality of dental implants. The method may include moving each of a plurality of extension members, and rotating each of a plurality of copings coupled to a corresponding extension member, to align each of the plurality of copings with a corresponding one of the plurality of dental implants. The method may also include locking the location and orientation of each coping with respect to a base, wherein the plurality of extension members are movably coupled to the base.

The locking step may comprise mechanically locking the location and orientation of each coping with respect to the base. In some embodiment, the locking step may comprise mechanically locking the location and orientation of each coping with respect to the base using a clamp. The method may also include, before locking the location and orientation of each coping with respect to the base, removably securing each coping to the corresponding one of the plurality of dental implants.

In at least one embodiment, the method may also include, after locking the location and orientation of each coping with respect to the base, disconnecting each coping from the corresponding one of the plurality of dental implants.

The method may also include, after disconnecting the copings, measuring the location and orientation of the plurality of implants by measuring a location and orientation of the plurality of copings.

Also, the method may include, after disconnecting the copings, connecting each coping to an implant analogue. Each implant analogue may be coupled to an implant analogue extension member. Also, each implant analogue extension member, may be coupled to a second base.

In at least one embodiment, the method may also include forming a negative impression by encasing the plurality of implants and at least a portion of each coping in impression material, and then separating the impression material and the copings together from the implants. Afterward, the method may include applying casting material to the negative impression to form a dental cast showing the implants.

In accordance with at least one embodiment, an apparatus is provided for replicating a location and orientation of each of a plurality of dental implants. The apparatus may include a base, and a plurality of extension members protruding from the base. Each of the plurality of extension members may be movable in relation to the base. Each extension member may include a proximal end connected to the base, a distal end, and a implant analogue connected to the distal end. The implant analogue may be movable in relation to a corresponding extension member. Furthermore, the implant analogue may be adapted to be mechanically locked in a selected location and orientation.

The apparatus may also include a plurality of clamps. Each of the plurality of clamps may be adapted to lock a corresponding extension member to the base. Also, each of the plurality of clamps may be adapted to lock a corresponding implant analogue in a selected location and orientation.

Each extension member may comprise an elongate upper portion and an elongate lower portion and each of the plurality of clamps may be adapted to urge one of the upper and lower portions toward the other of the upper and lower portions of a corresponding extension member.

Each implant analogue may be at least partially received in a corresponding spherical member. Also, each of the plurality of clamps may be adapted to urge the upper and lower portions of the corresponding extension member against an external surface of the corresponding spherical member to lock a location and orientation of the corresponding spherical member with respect to the extension member.

Each implant analogue may be at least partially received in a through-hole of the corresponding spherical member. The through-hole may be defined by an interior surface of the spherical member. Each of the plurality of clamps may be adapted to urge the upper and lower portions of the corresponding extension member against the external surface of the corresponding spherical member to reduce a diameter of the through-hole of the corresponding spherical member thereby urging the interior surface of the corresponding spherical member against the corresponding implant analogue. This may lock the location and orientation of the implant analogue with respect to the base.

The implant analogue may be connected to the corresponding extension member by a ball joint.

In at least one embodiment, the base may include at least one slot. Also, each of the plurality of clamps may pass through one of the at least one slot, and each of the plurality of clamps may be adapted to lock the corresponding extension member relative to the corresponding slot.

A location and orientation of each implant analogue may be fixed with respect to the corresponding extension member. However, each implant analogue may be rotatable with respect to the corresponding extension member in at least two orthogonal axes. Also, each clamp may be adapted to resist rotation of the corresponding implant analogue relative to the corresponding extension member.

At least one extension member may be translatable along a plane, and each extension member may be rotatable about an axis perpendicular to the plane. The axis may be concentric with the corresponding clamp.

DRAWINGS

FIG. 25 is a partial cross-sectional view taken along line G-G of FIG. 24 showing the impression device of FIG. 22 secured to the framework of FIG. 20 in accordance with at least one embodiment;

DESCRIPTION OF VARIOUS EMBODIMENTS

As used herein, the term "location" refers to an object's linear position, and the term "orientation" refers to an object's angular position. Specifically the location of an object is described by the object's position along three perpendicular axes (e.g. x, y, z) and the object's orientation is described by the object's rotation about these three axes.

Figure 1:
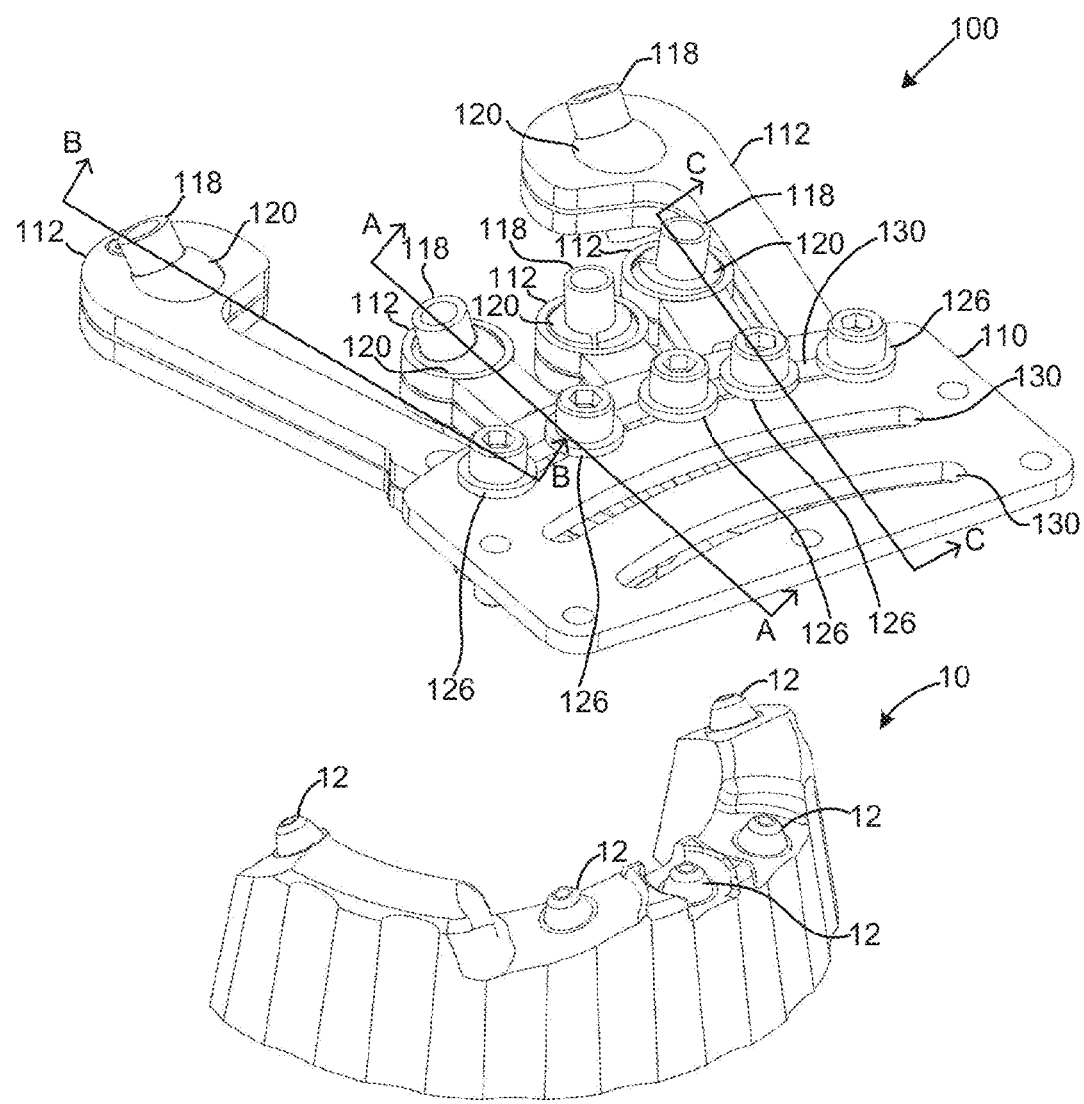
FIG. 1 is a perspective view of an impression device and a jawbone in accordance with at least one embodiment.

FIG. 1 shows a perspective view of a jawbone 10 and an impression device 100 in accordance with at least one embodiment of the apparatus for measuring the location and orientation of dental implants. In the example shown, impression device 100 includes a base 110, and five extension members 112 protruding from base 110.

Impression device 100 may be manufactured from any one or more of a number of suitable materials. For example, impression device 100 may include metal, plastic, ceramics and elastomers. In at least one embodiment, impression device 100 has a substantially rigid construction.

In at least one embodiment, impression device 100 may include fewer or greater than five extension members 112. For example, impression device 100 may include from one to ten extension members 112. Furthermore, although the example shows only two lengths of extension members 112 (two long and three short), in accordance with some embodiments there may be any distribution of lengths of extension members 112. For example, impression device 100 may include extension members 112 all having the same length, or extensions members 112 all having different lengths.

Figure 2:
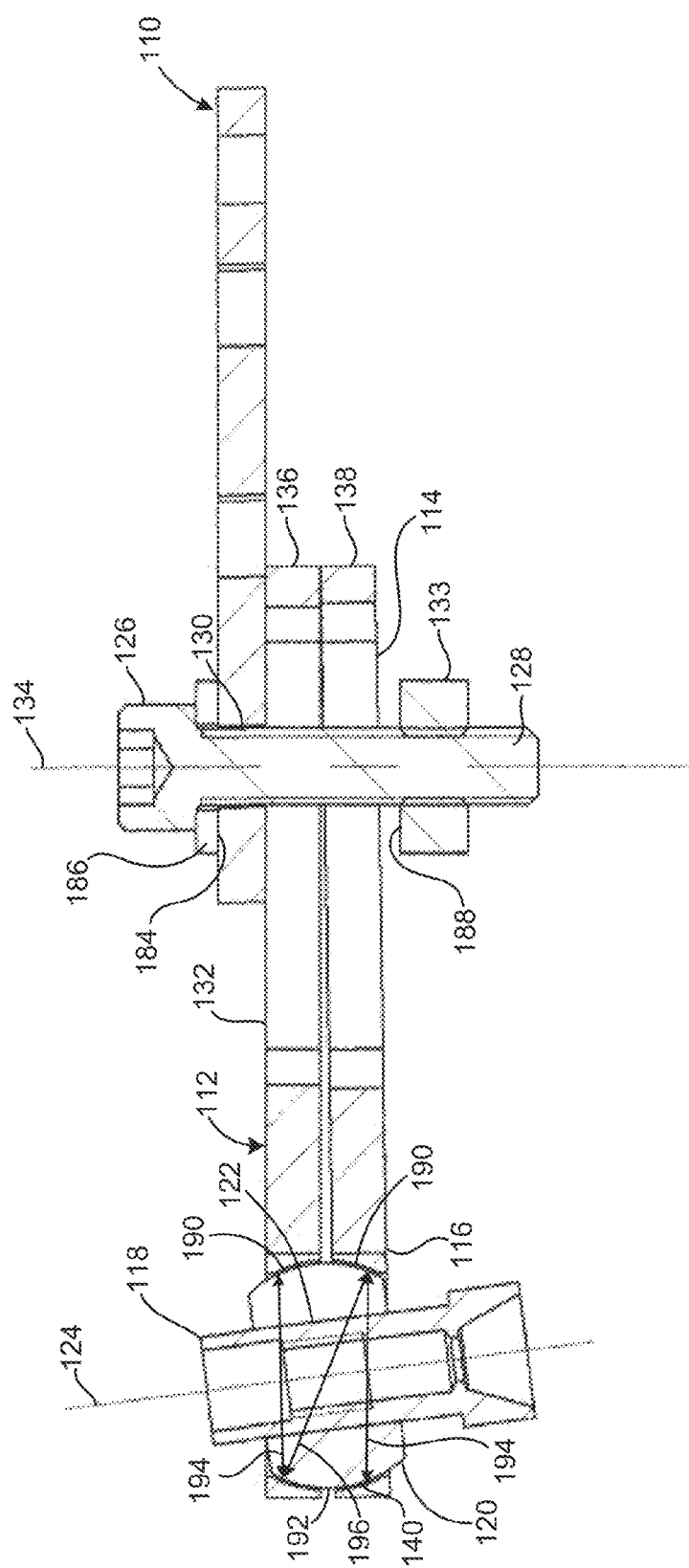
FIG. 2 is a partial cross-sectional view taken along line A-A of FIG. 1 in accordance with at least one embodiment.

Referring to FIG. 2, each extension member 112, has a proximal end 114 connected to base 110, and a distal end 116. A coping 118 is connected to the distal end 116 of each extension member 112. In at least one embodiment, each coping 118 may rotate about at least two orthogonal axes with respect to the corresponding extension member 112. In alternative embodiments, one or more copings 118 may rotate about three orthogonal axes (e.g. pitch, yaw, and roll) with respect to the corresponding extension member 112.

In at least one embodiment, a coping 118 may be connected to distal end 116 of an extension member 112 by a ball joint. In the example shown, a coping 118 is connected to the distal end 116 of each extension member by a spherical member 120. Spherical member 120 may include a through-hole 122 in which a respective coping 118 is received. In some embodiments, through-hole 122 may be sized to permit a coping 118 inserted therein to move along the longitudinal axis 124 of the through-hole 122.

Although through-hole 122 has a circular cross-section in the example shown, in at least one embodiment, through-hole 122 may have a different cross-sectional profile such as a square or irregular cross-section, for example. Moreover, the cross-sectional profile of through-hole 122 may vary along its length in at least one embodiment.

Figure 3:
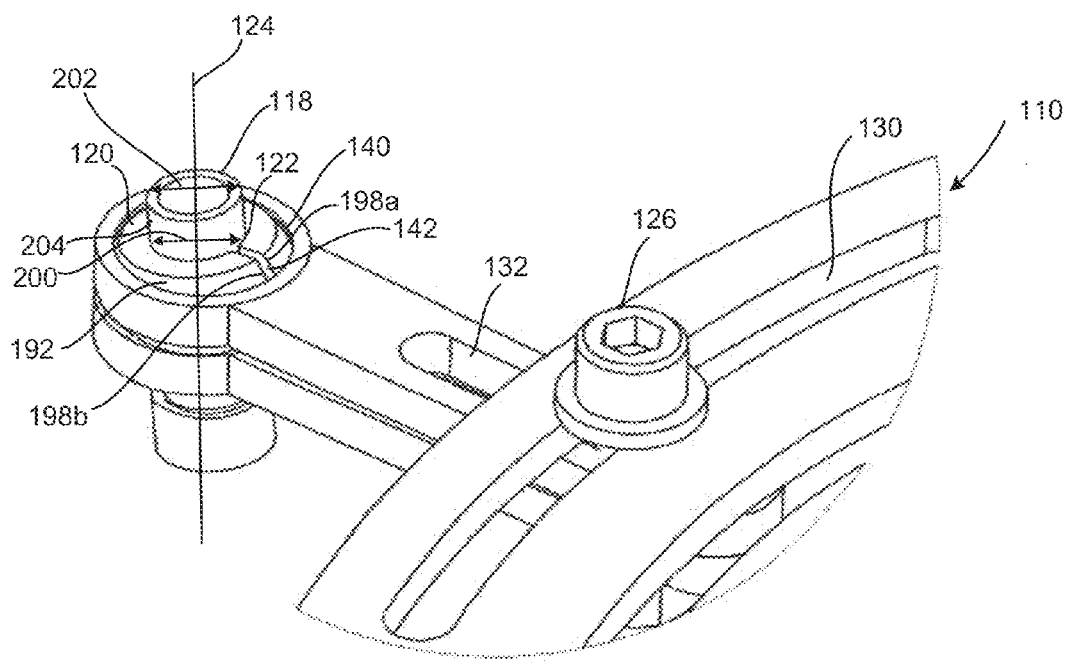
FIG. 3 is a partial perspective view of the impression device of FIG. 1 in accordance with at least one embodiment.

Referring now to FIGS. 2 and 3, in the example shown, each extension member 112 is connected to base 110 by a clamp 126. Generally, a clamp 126 may be engaged to lock the location and orientation of the corresponding extension member 112 with respect to base 110.

When a clamp 126 is not engaged, the corresponding extension member 112 may move and rotate relative to the base 110. In the example shown, an extension member 112 may rotate about a longitudinal axis 134 of the corresponding clamp 126, and move in a plane perpendicular to that axis 134. In some embodiments, each extension member 112 may include more or less freedom of movement when the respective clamp 126 is disengaged.

In the example shown, clamp 126 includes a threaded bolt 128 which extends through an opening 130 in base 110 and an opening 132 in a respective extension member 112. Base 110 is shown with three openings 130, configured as slots. Slots 130 permit each extension member 112 to be selectively coupled to base 110 at a selected position along one of the slots 130.

In some embodiments, base 110 may include fewer or greater openings 130. For example, base 110 may include one slot 130 through which all bolts 128 are inserted. Alternatively, base 110 may include a different one opening 130 for each bolt 128. Where base 110 includes one or more slots 130, they may be curved as shown, straight or follow another suitable path.

Extension members 112 are shown each having an opening 132 configured as a slot. Slot 132 allows the protrusion length of the respective extension member 112 to be adjusted. In the example shown, bolt 128 may be selectively positioned along a respective slot 132 for connecting extension member 112 to base 110 at the selected position. In some embodiments, each opening 132 may be configured as a singular hole, a plurality of holes, or a plurality of slots.

In some embodiments, there may be no openings 130 or 132. For example, clamps 126 may be configured as a C-clamp which does not need to pass through the objects that it clamps.

In the example shown, a clamp 126 includes a bolt 128 with external threads along its shank that mate with the internal threads of a nut 133. The clamp 126 may be engaged by tightening nut 133 until a lower surface 184 of washer 186 and an upper surface 188 of nut 133 apply a compressive force onto base 110 and the respective extension member 112. The compressive force may increase friction between the respective extension member 112 and base 110 thereby locking the location and orientation of the respective extension member 112 with respect to base 110. In at least some embodiments, where clamp 126 is configured differently (e.g. as a C-clamp), clamp 126 may be engaged by a different mechanism.

In the example shown, each extension member 112 has an upper portion 136 and a lower portion 138. Opening 132 extends through both the upper and lower portions 136, 138. Generally, engaging clamp 126 may move the respective upper and lower portions 136, 138 closer to each other such that they are in close proximity (or in an abutting relationship).

At the distal end of extension member 112, the spherical member 120 is shown positioned in a through-hole 140 which extends through both the upper and lower portions 136, 138. As shown, through-hole 140 is defined by surfaces 190 of the upper and lower portions 136, 138. Surfaces 190 may be arranged so that when the upper and lower portions 136, 138 are brought together by engagement of the respective clamp 126, surfaces 190 bear upon exterior 192 of the spherical member 120. In the example shown, surfaces 190 have a concave shape that corresponds to the shape of spherical member 120. Preferably, this permits spherical member 120 and through-hole 140 to interact as a spherical joint. In alternative embodiments, through-hole 140 may have a spherical, conical cylindrical or complex shape, for example.

In the example shown, surfaces 190 are arranged such that when upper and lower portions 136, 138 abut at distal end 116, a distance 194 between points of contact is equal to or less than a diameter 196 of the spherical member 120. For example, distance 194 may be from about 0% to 80% smaller than diameter 196 when upper and lower portions 136, 138 abut at distal end 116. That is, when upper and lower portions 136, 138 abut at distal end 116, through-hole 116 is too small for spherical member 120 to fit inside. Therefore, surfaces 190 bear upon exterior 192 of spherical member 120 when upper and lower portions 136, 138 are compressed together by the respective clamp 126. This increases friction between extension member 112 and spherical member 120 at the interfaces of exterior 192 of spherical member 120 and surfaces 190. This increased friction effectively locks the location and orientation of spherical member 120 with respect to the respective extension member 112 by preferably preventing movement of the spherical member 120.

Figure 4:
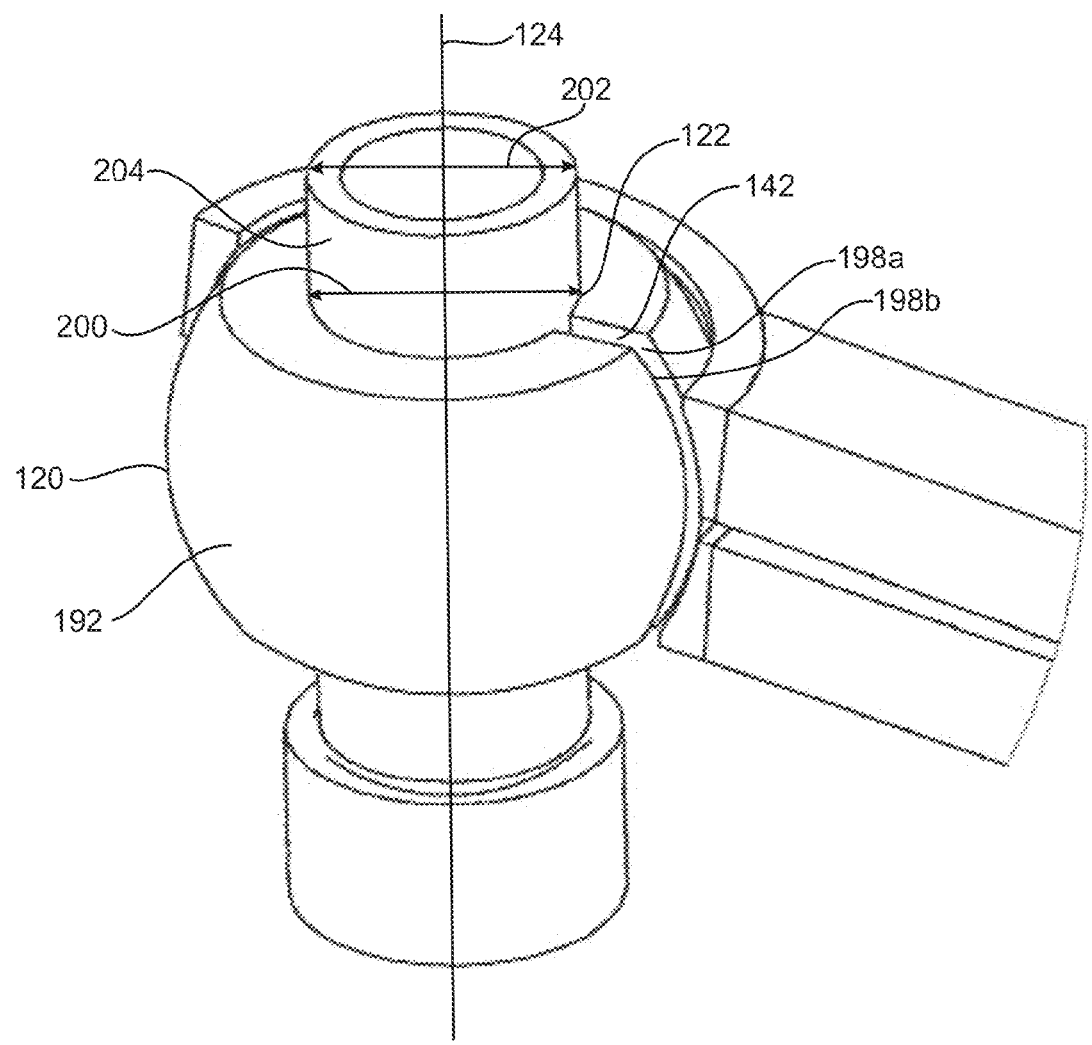
FIG. 4 is a partial perspective cut-away view of the impression device of FIG. 1 in accordance with at least one embodiment.

Referring now to FIGS. 3 and 4, spherical member 120 is shown having a slit 142 defined by opposing surfaces 198a and 198b. Slit 142 and through-hole 124 cause spherical member 120 to have a "C" shape when viewed from above along longitudinal axis 124. Upon application of force on exterior 192, the gap between opposing surfaces 198a and 198b may be reduced. In the example shown, surfaces 190 of the corresponding extension member 112 may apply this force when clamp 126 compresses the upper and lower portions 136, 138 together.

When clamp 126 compresses upper and lower portions 136, 138 causing surfaces 190 of the respective extension member 112 to bear upon exterior 192 of spherical member 120, opposing surfaces 198a and 198b may move toward each other. In the example shown, if opposing surfaces 198a and 198b were to meet, the diameter 200 of through-hole 122 would be reduced to less than the diameter 202 of coping 118. Therefore when the gap between opposing surfaces 198a and 198b is reduced, the space between the internal surfaces (not shown) that define through-hole 122, and exterior 204 of coping 118 may be substantially eliminated. This increases friction between the internal surfaces that define through-hole 122 and exterior 204 of coping 118 thereby producing a tight fit. This increased friction effectively locks the location and orientation of coping 118 with respect to the corresponding spherical member 120.

As described in detail above, engaging clamp 126 may lock the location and orientation of:
  (i) one or more extension members 112 with respect to base 110;
  (ii) spherical member 120 with respect to the corresponding extension member 112; and
  (iii) coping 118 with respect to the corresponding spherical member 120.

Therefore, in the example shown, engaging clamp 126 may effectively lock the location and orientation of coping 118 with respect to base 110.

Figure 5:
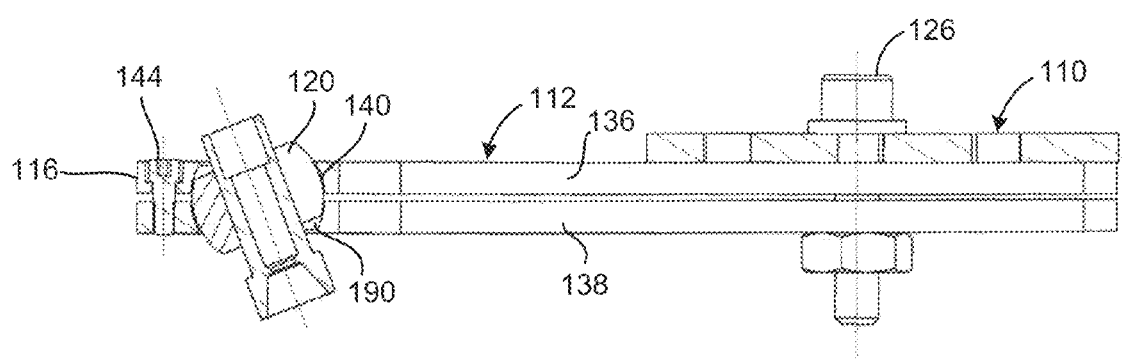
FIG. 5 is a partial cross-sectional view taken along line B-B of FIG. 1 in accordance with at least one embodiment.
Figure 6:
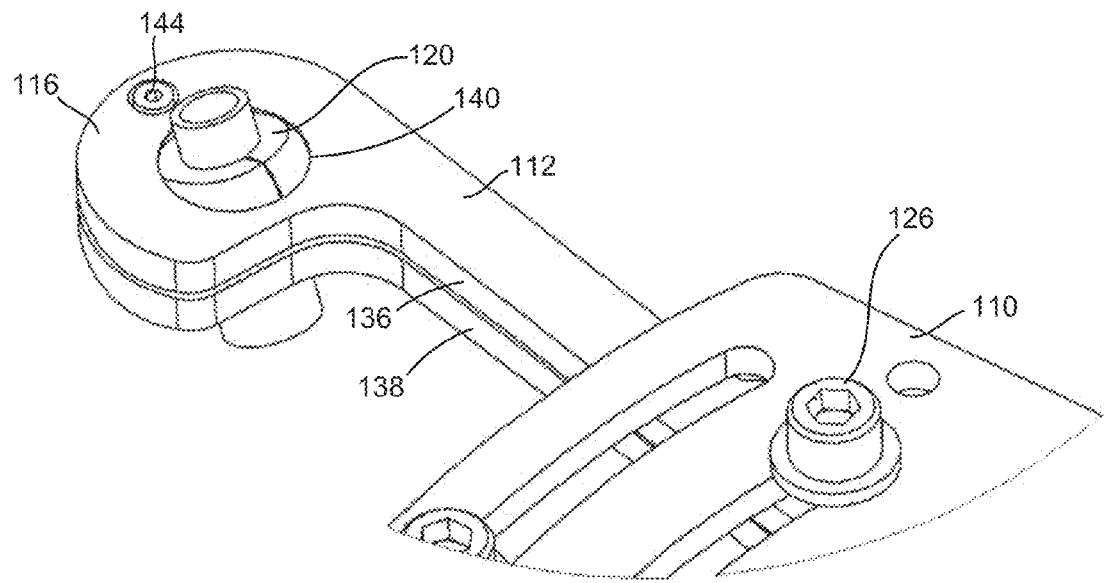
FIG. 6 is a partial perspective view of the impression device of FIG. 1 in accordance with at least one embodiment.

Referring now to FIGS. 5 and 6, depending on the thickness, material and length of an extension member 112, there is a risk that when clamp 126 is engaged extension member 112 may deform or bend against the resistance of spherical member 120. This may result in an interference fit between spherical member 120 and surfaces 190 that define through-hole 140, which is ineffective for locking the location and orientation of the respective coping 118 with respect to base 110. Therefore, an extension member 112 may be configured with a screw 144 to retain the distal end 116 of the upper and lower portions 136, 138 in close proximity (or in abutting relationship). As clamp 126 is engaged, the upper and lower portions 136, 138 may pivot toward each other about screw 144, which may act similarly to a hinge.

The upper and lower portions 136, 138 of extension member 112 may alternatively be connected at the distal end 116 by another mechanism, such as a clamp, a bolt, a hinge, a weld, an elastic band, adhesive or by integrally molding the upper and lower portions 136, 138 at the distal end 116. In some embodiments, the upper and lower portions 136, 138 may be separated by a predetermined gap at distal end 116 using, for example, a shim or surgery thread.

Figure 7:
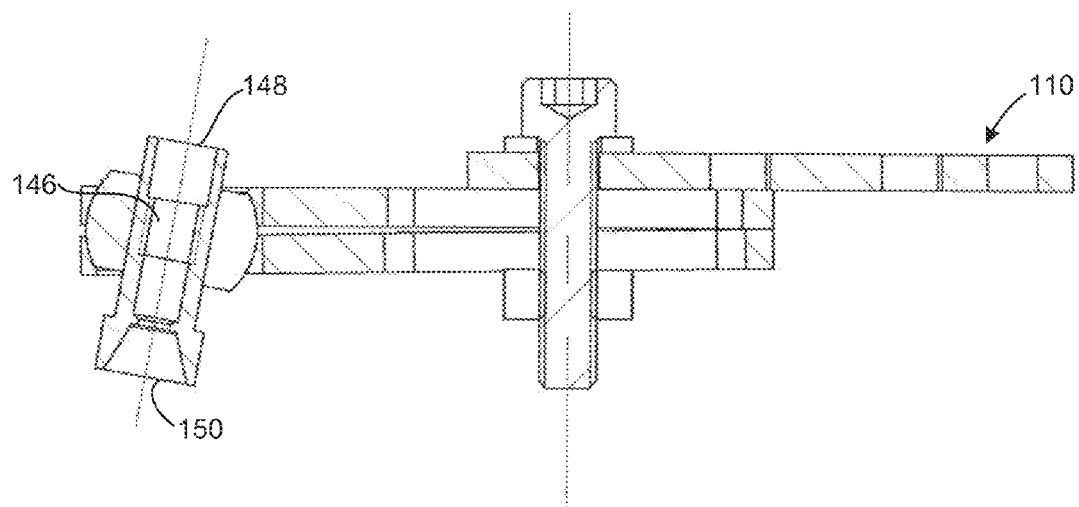
FIG. 7 is a partial cross-sectional view taken along line C-C of FIG. 1 showing an engaged clamp in accordance with at least one embodiment.

Referring to FIG. 7, coping 118 has a through-hole 146. Through-hole 146 has an upper portion 148 and a lower recess 150. Lower recess 150 is shaped to receive an implant 12 (see FIG. 1). In the example shown, lower recess 150 has a shape that is a negative impression of an implant 12.

A method 300 for making a dental framework will now be described with reference to FIGS. 1-8.

At step 302, clamps 126 are not engaged and each coping 118 is aligned with a corresponding implant 12. Coping 118 may have up to six degrees of freedom with respect to base 110. In the example shown, coping 118 can move about a horizontal plane because coping 118 is coupled to extension member 112 that can move about the horizontal plane with respect to base 110 as described above. Coping 118 can also rotate about at least two perpendicular axes because coping 118 is coupled to spherical member 120 that can rotate about the at least two perpendicular axes with respect to extension member 112 as described above. In at least one embodiment, coping 118 and spherical member 120 can rotate about three perpendicular axes (e.g. pitch, yaw and roll) with respect to extension member 112. Coping 118 can also move along longitudinal axis 124, as described above. This freedom of movement may permit lower recess 150 to be precisely mated with a respective implant 12.

Figure 9:
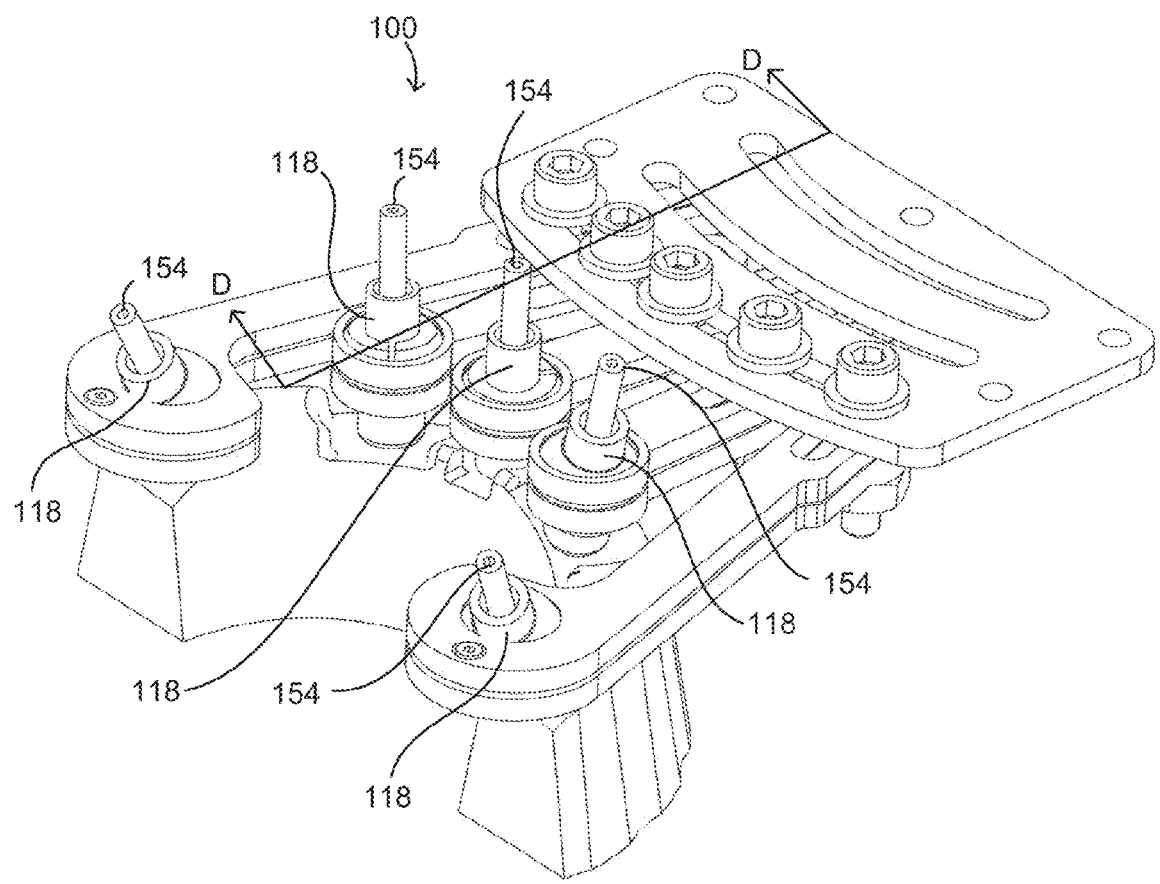
FIG. 9 is a perspective view of the impression device of FIG. 1 secured to a plurality of implants in the jawbone in accordance with at least one embodiment.

At step 304, an impression screw 154 may be inserted into through-hole 146 and secured to implant 12. FIG. 9 shows impression device 100 having an impression screw 154 inserted into each coping 118. Securing impression screw 154 onto implant 12 may effectively lock the location and orientation of the respective coping 118 with respect to the implant 12. Impression screw 154 may be substituted by a different fastener that is compatible with the implant 12.

Figure 10:
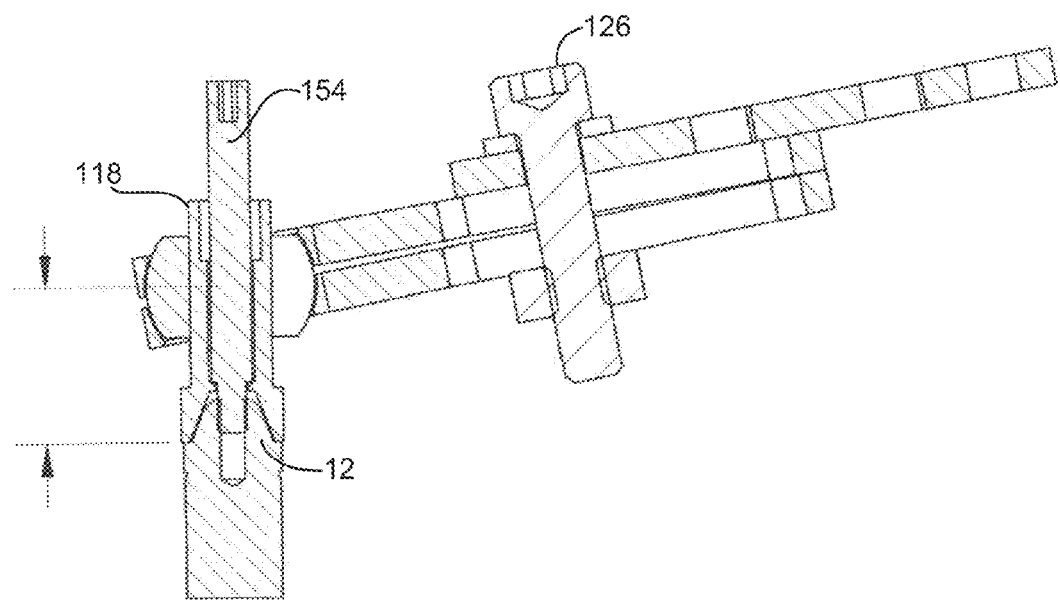
FIG. 10 is a partial cross-sectional view taken along line D-D of FIG. 9 in accordance with at least one embodiment.

At step 306, clamps 126 are engaged thereby locking a location and orientation of each coping 118 to base 110. FIG. 10 shows an engaged clamp 126 with a coping 118 secured to an impression screw 154 that is secured to an implant 12. In at least one embodiment, locking the location and orientation of coping 118 with respect to the respective implant 12 may prevent the coping 118 from losing alignment with the implant 12 while or after clamp 126 is secured.

At step 308, impression screws 154 are removed from implants 12, thereby decoupling copings 118 from the corresponding implants 12.

Those skilled in the art will understand that method steps 302, 304, 306 and 308 may be performed for each coping 118.

After all copings 118 have been decoupled from the respective implants, impression device 100 may be removed from a patient's mouth at step 310.

Figure 11:
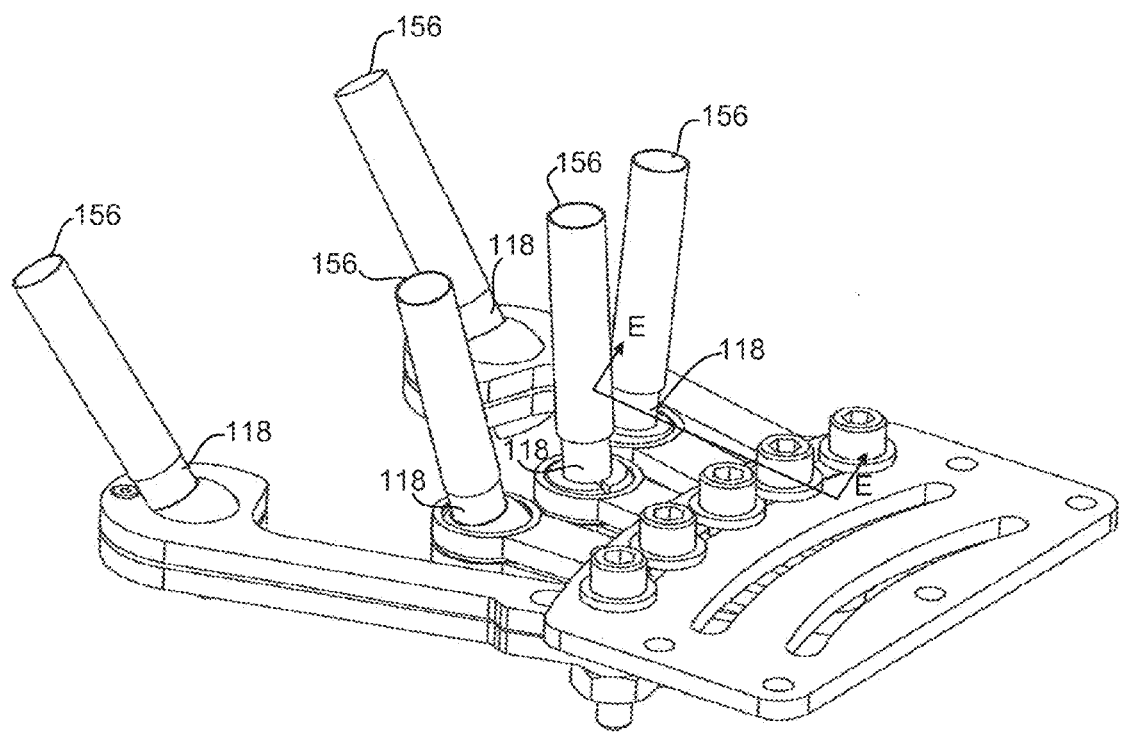
FIG. 11 is a perspective view of the impression device of FIG. 1 having measurement targets secured thereto in accordance with at least one embodiment.
Figure 12:
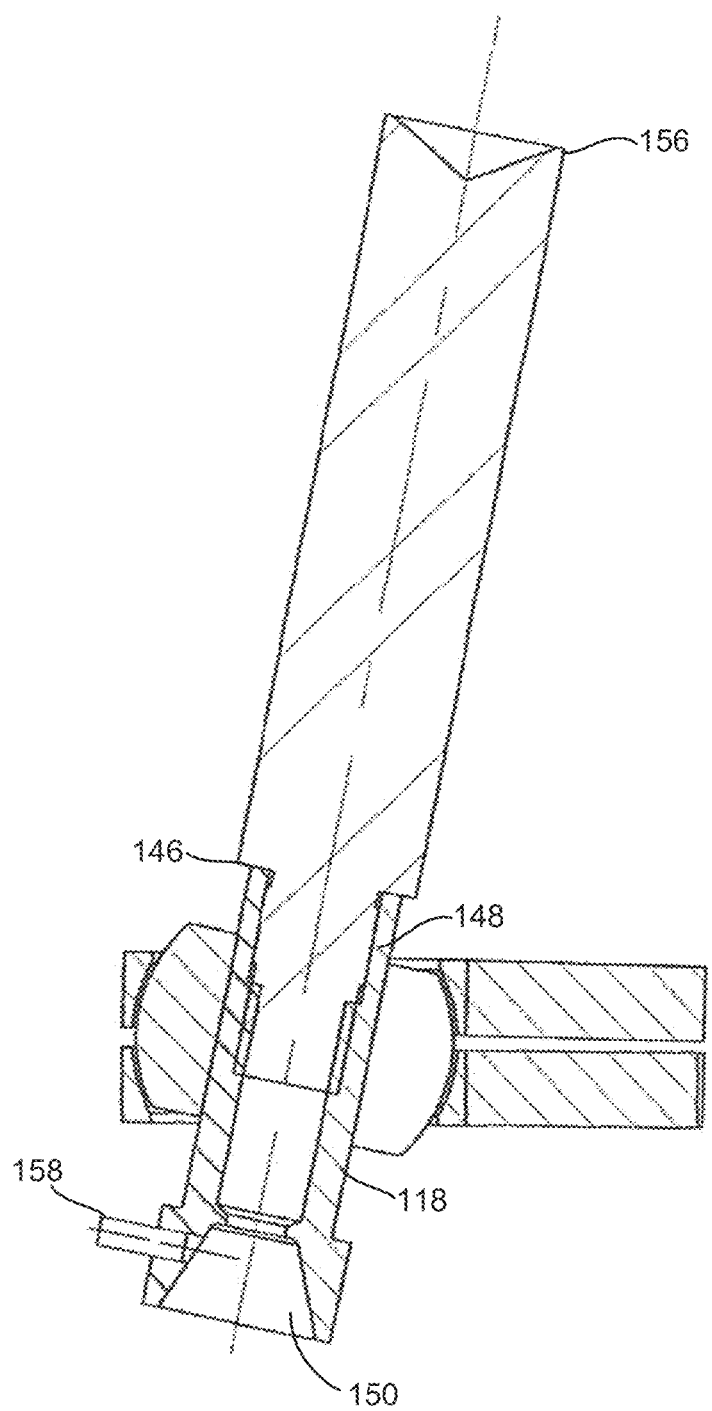
FIG. 12 is a partial cross-sectional view taken along line E-E of FIG. 11 in accordance with at least one embodiment.

At step 312, a measurement system (not shown), including for example a coordinate measurement device, may be used to measure the location and orientation of the copings 118 with respect to base 110, which are mechanically locked in position by clamps 126. FIGS. 11 and 12 show coping 118 having measurement targets 156 inserted into the upper portion 148 of through-hole 146. Generally, the measurement system may capture the location and orientation of the measurement targets 156 from which the location and orientation of the coping 118 may be determined.

In accordance with at least one embodiment, through-hole 146 is internally threaded and measurement targets 156 include screws for securing the measurement targets 156 in the through-hole 146. A measurement target 156 may alternatively be secured to a coping 118 by welding, adhesive, interference fit, or by integrally molding a measurement target 156 with a coping 118, for example.

A coping 118 may be provided with more than one measurement target 156. In some cases, providing additional measurement targets may improve the accuracy of measurements taken by a measurement system capturing the targets 156. As shown in FIG. 12, a secondary measurement target 158 may be provided near the lower recess 150 of coping 118. In at least one embodiment, the rotation of coping 118 about its longitudinal axis 124 (i.e. roll) may be measured more accurately using a secondary measurement target 158.

Although FIGS. 11 and 12 show cylindrical measurement targets 156, 158, any type of measurement target 156, 158 that is compatible with the measurement system may be used. In at least one embodiment, the measurement system may measure the copings 118 themselves without the need for any measurement targets 156, 158 at all.

In some cases, the location of a patient's implants 12 may make it difficult to secure a coping 118 to every implant 12 at the same time. For example, two implants 12 may be positioned so close to one another that interference between the two respective extension members 112 prevents the two respective copings 118 from being aligned with those implants 12.

Therefore, in accordance with at least one embodiment, the location and orientation of a subset of implants 12 may be determined separately from another subset. For example, by including the same implant 12 across subsets, that implant 12 may be used as a reference point to combine the measurements of the different subsets. This is illustrated by FIGS. 27 and 28.

Figure 27:
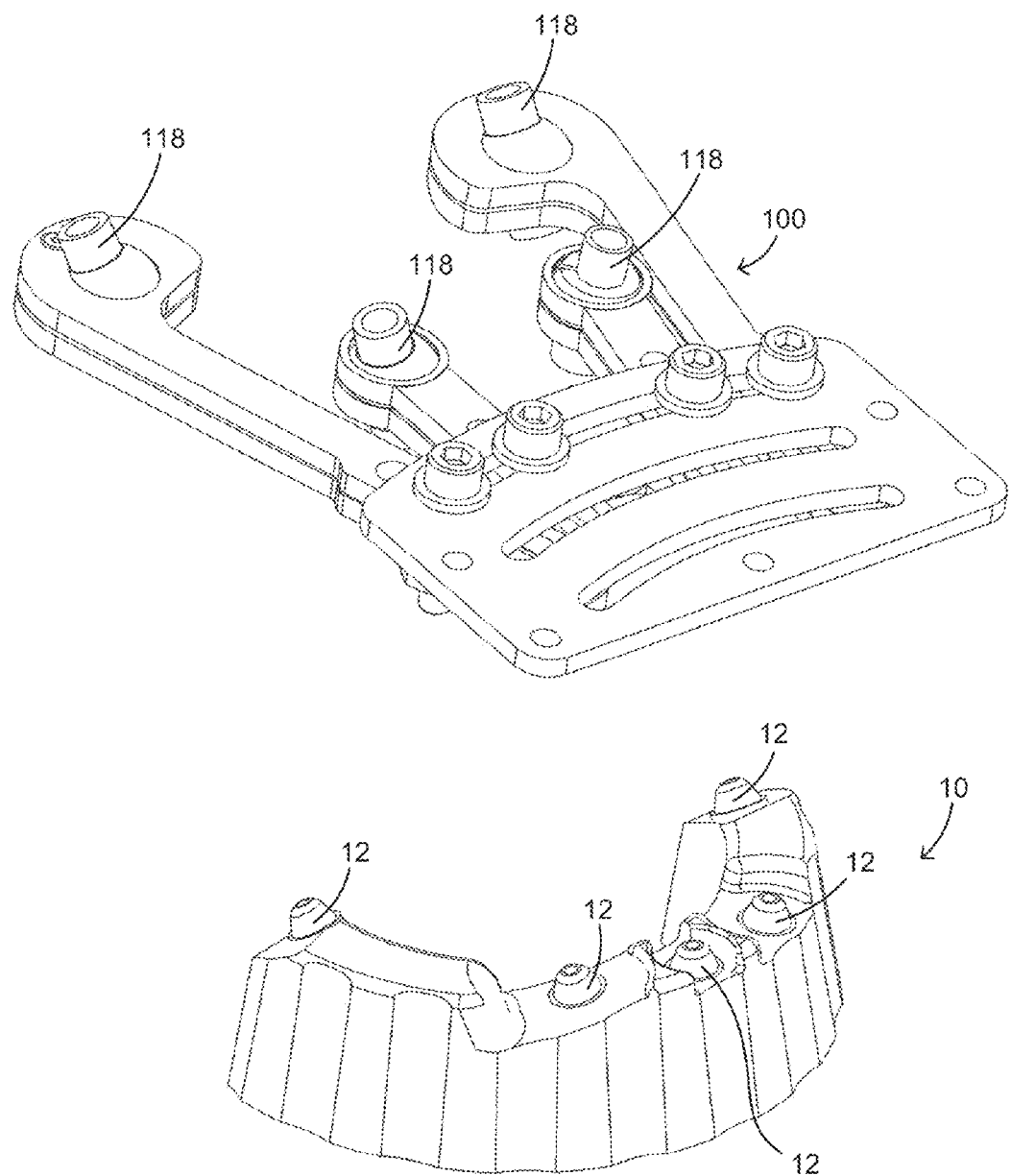
FIG. 27 is a perspective view of an impression device having four copings and a jawbone having five implants in accordance with at least one embodiment.
Figure 28:
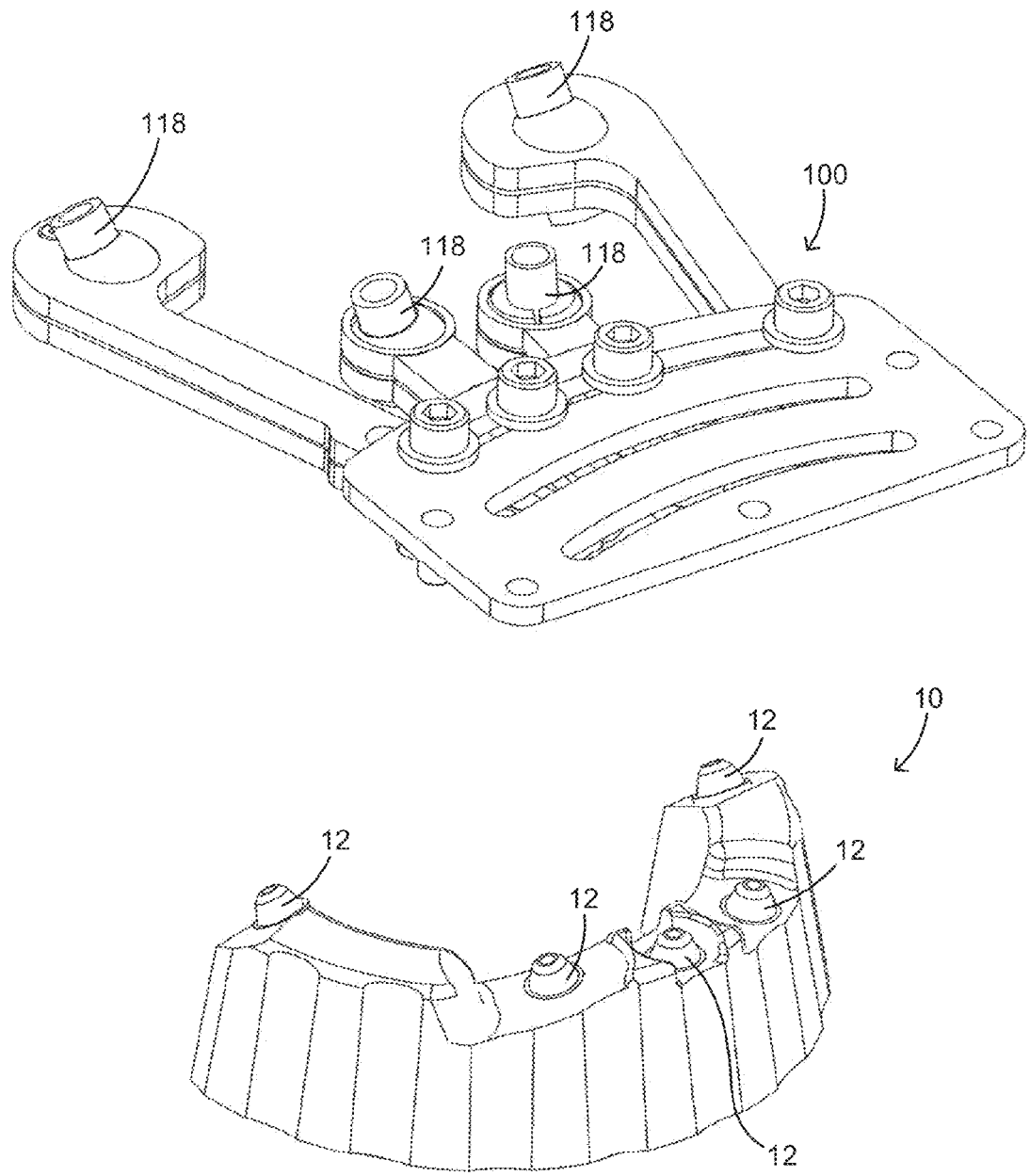
FIG. 28 is a perspective view of an impression device having four copings and a jawbone having five implants in accordance with at least one embodiment.

FIGS. 27 and 28 show an impression device 100 configured with four copings 118 for measuring a location and orientation of four out of five implants 12 in a jawbone 10. The copings 118 are shown aligned with different implants 12 in FIG. 27 than in FIG. 28. However, three out of five copings 118 are aligned with the same implants 12 in both FIGS. 27 and 28. These copings 118 may serve as reference points for combining the two sets of measurements of four implants 12 into a single set of measurements of all five implants 12.

In accordance with at least one embodiment, a jawbone cast may be made at step 314 in addition or as an alternative to measuring the impression device 100 at step 312.

Figure 8:
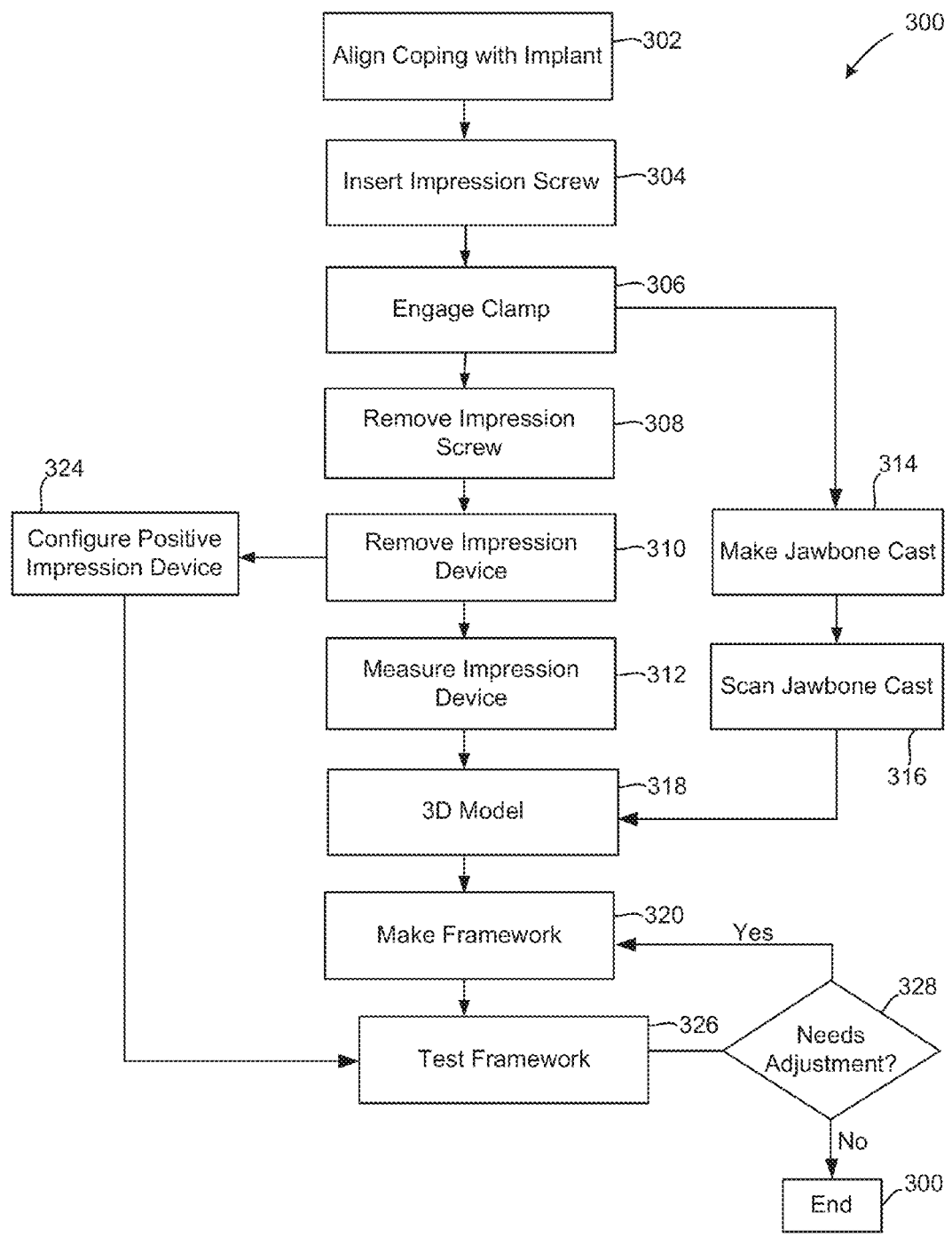
FIG. 8 shows a flowchart illustrating a method for making a dental framework in accordance with at least one embodiment.
Figure 13:
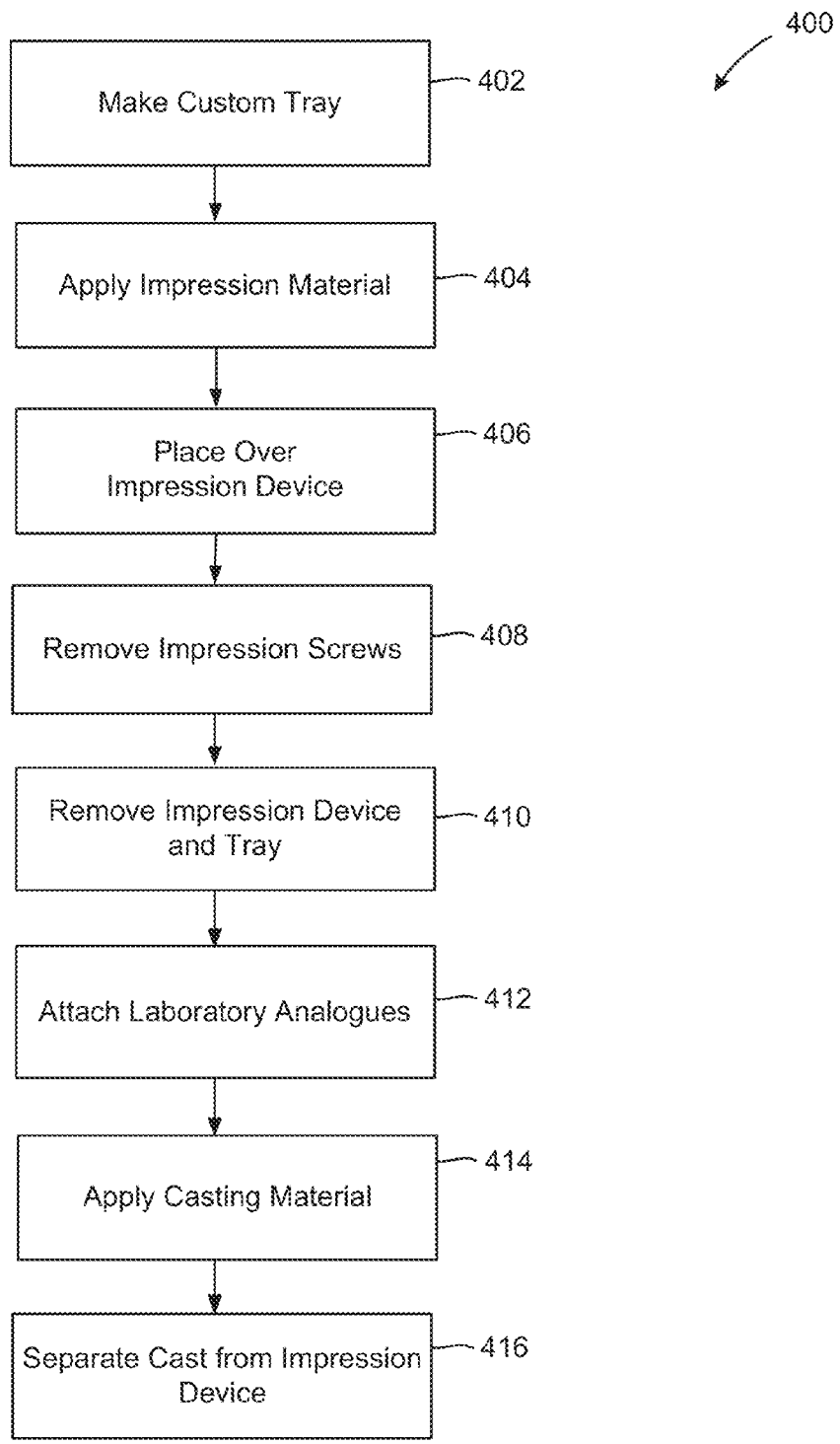
FIG. 13 shows a flowchart illustrating a method for casting a jawbone to make a jawbone cast in accordance with at least one embodiment.
Figure 14:
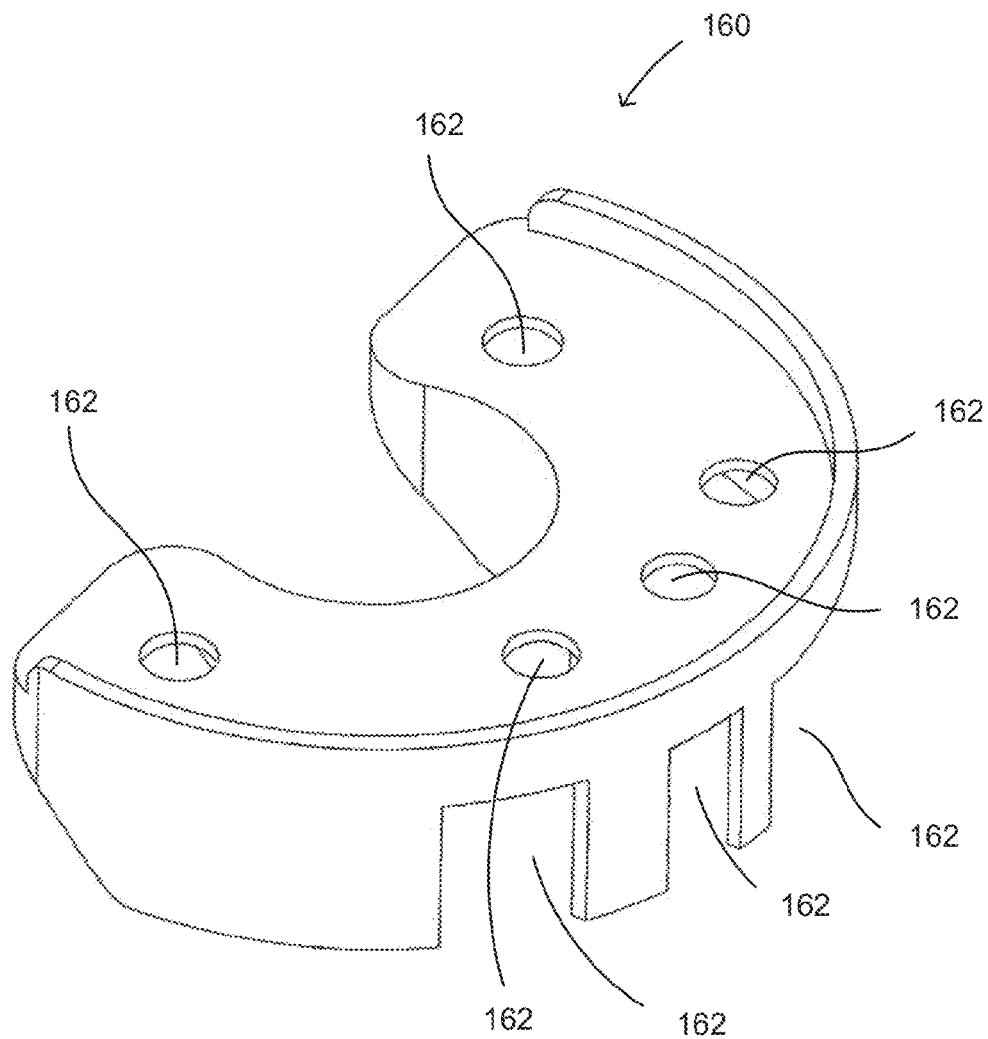
FIG. 14 is a perspective view of a custom impression tray in accordance with at least one embodiment.

FIG. 13 shows a flowchart illustrating a method 400 for casting a jawbone to make a jawbone cast (step 314 in FIG. 8). At step 402 a custom impression tray may be made. FIG. 14 shows an example of a custom impression tray 160 including openings 162 for receiving various parts of impression device 100.

Figure 15:
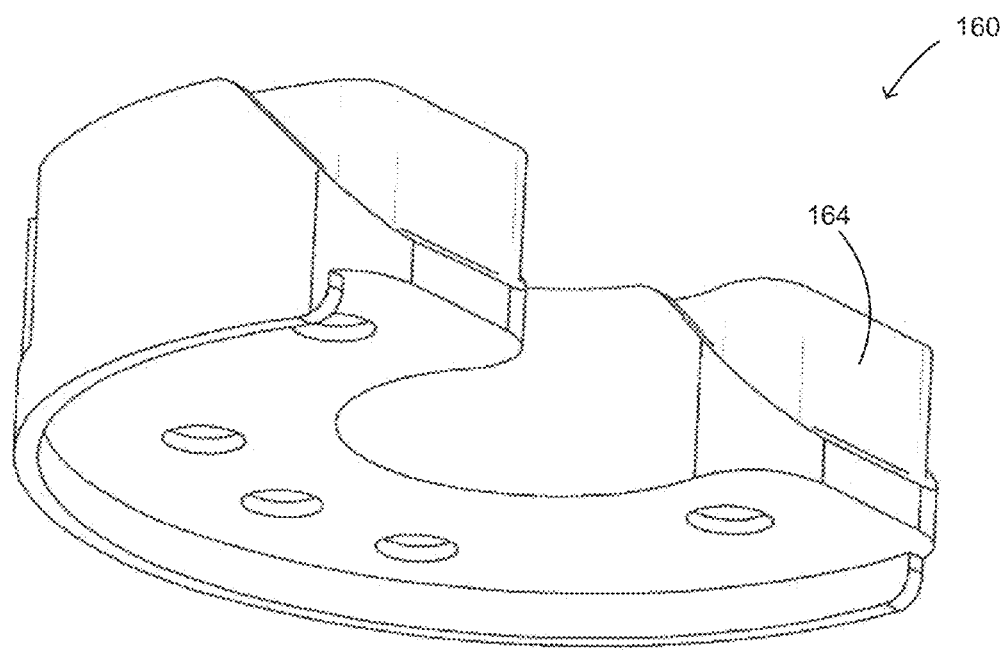
FIG. 15 is a perspective view of a custom impression tray including impression material in accordance with at least one embodiment.

At step 404, impression material may be applied inside custom impression tray 160. FIG. 15 shows custom impression tray 160 filled with impression material 164.

Figure 16:
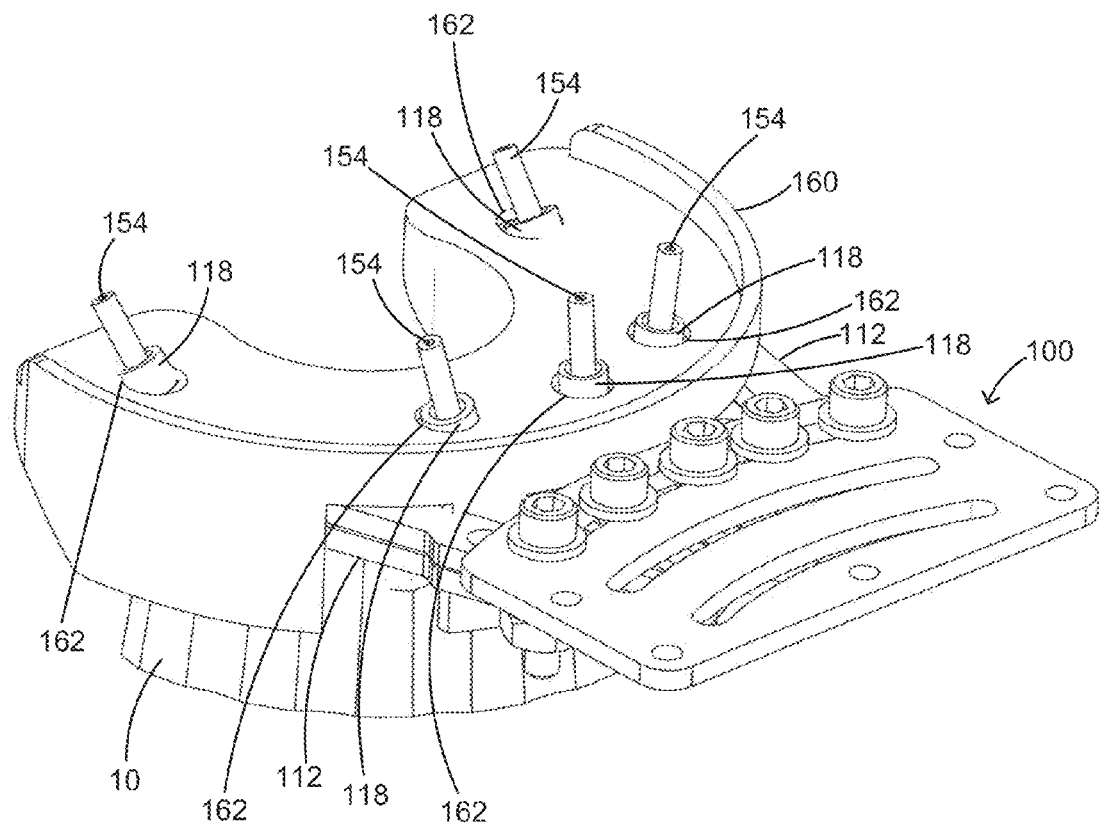
FIG. 16 is a perspective view of the impression device and jawbone of FIG. 9 having the custom impression tray of FIG. 15 applied thereto in accordance with at least one embodiment.

At step 406, custom impression tray 160, including impression material 164 may be placed over top of impression device 100, which is secured to jawbone 10 using impression screws 154. As shown in FIG. 16, various components of impression device 100, such as impression screws 154 and extension members 112, may extend through the openings 162 in the custom impression tray 160.

Depending on the type of impression material 164, custom impression tray 160 may be kept in the place over jawbone 10 until the impression material 164 has set or has been cured (e.g. by ultra-violet light). In at least one embodiment, strips of flexible material (not shown), such as plastic for example, may be applied to custom impression tray 160 to prevent impression material 164 from escaping through openings 162. Afterwards, impression screws 154 may be removed at 408 to decouple impression device 100 and custom impression tray 160 from jawbone 10. Next, impression device 100 and custom impression tray 160 including impression material 164 may be removed from the jawbone and the patient's mouth at step 410.

Figure 17:
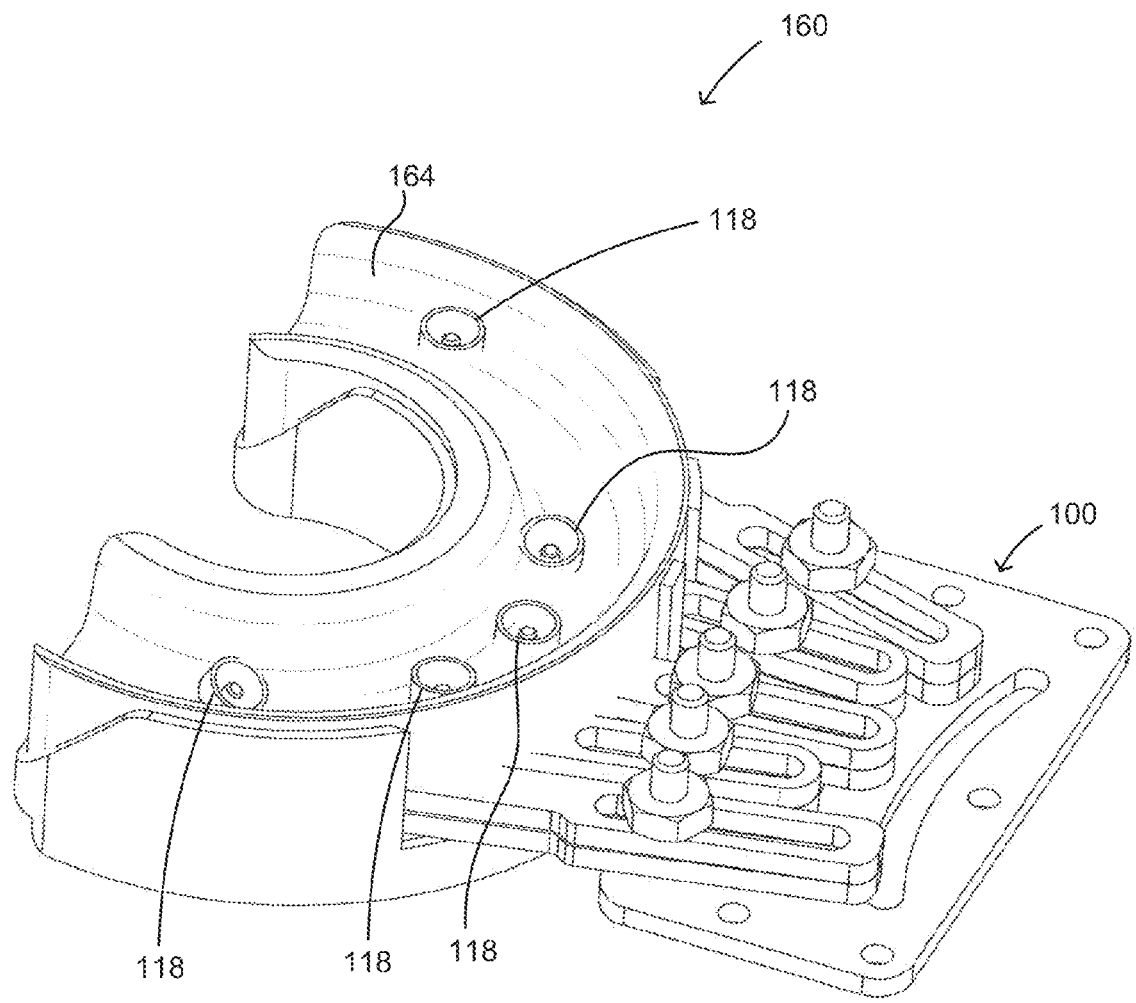
FIG. 17 is a perspective view of the custom impression tray of FIG. 14 after taking an impression of the dentition of the jawbone of FIG. 16 in accordance with at least one embodiment.

FIG. 17 shows impression device 100, along with custom impression tray 160 and impression material 164 after they have been removed from the patient's mouth. In the example shown, copings 118 continue to protrude through impression material 164.

Figure 18:
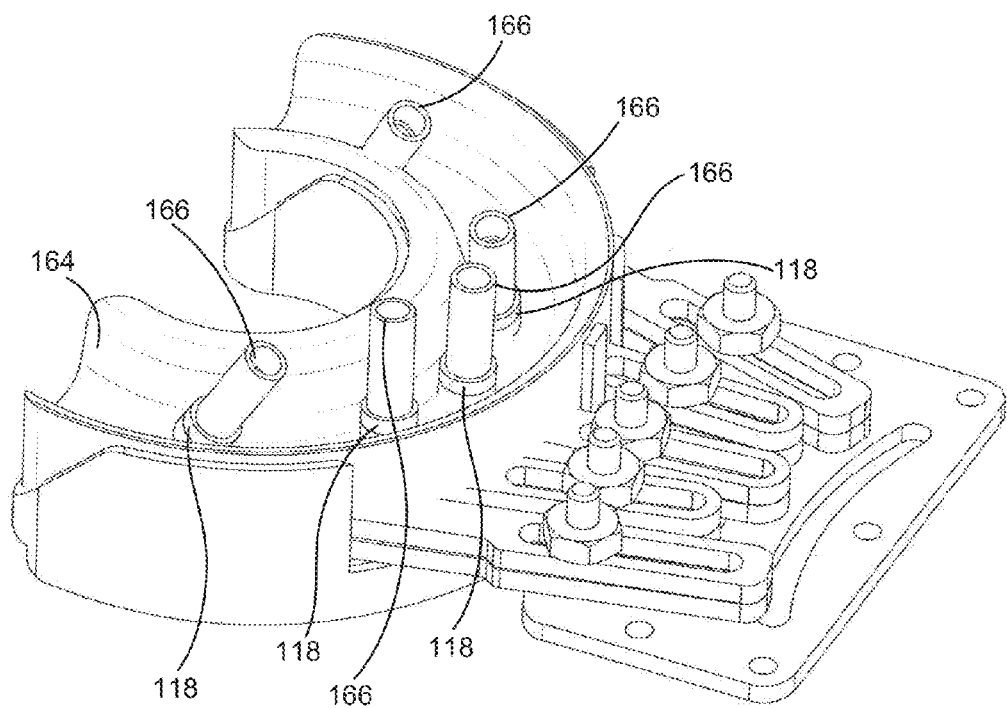
FIG. 18 is a perspective view of the custom impression tray of FIG. 17 having laboratory analogues secured thereto in accordance with at least one embodiment.
Figure 19:
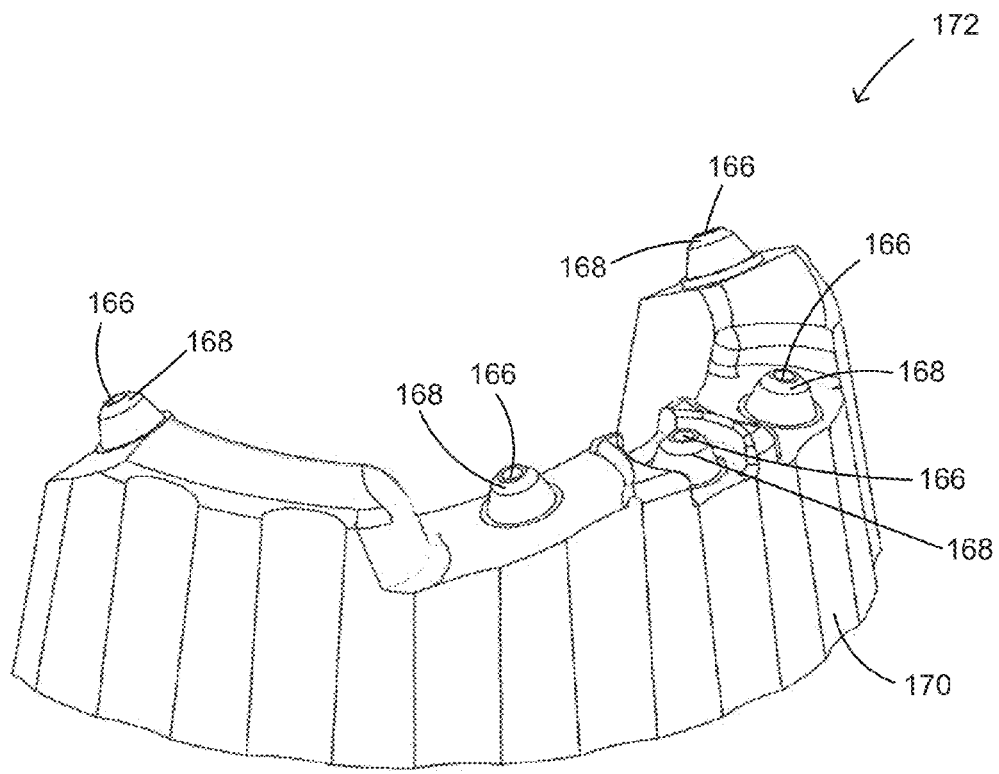
FIG. 19 is a perspective view of a jawbone cast in accordance with at least one embodiment.

At step 412, a laboratory analogue 166 may be attached to each coping 118, as shown in FIG. 18. As shown in FIG. 19, each laboratory analogue 166 has an interface 168 that is analogous to the respective implant 12.

At step 414, casting material 170 (e.g. dental stone material) may be poured onto the impression material 164. After the casting material 170 has set or is cured into a jawbone cast 172, the jawbone cast 172 may be separated from the impression device 100, at step 416.

FIG. 19 shows a jawbone cast 172 that may be made according to method 400. In the example shown, jawbone cast 172 includes laboratory analogues 166 whose interfaces 168 protrude from the casting material 170. Jawbone cast 172 may provide an accurate representation of a patient's jawbone including precisely located and oriented implant interfaces 168.

Returning to FIG. 8 and method 300, at step 316 jawbone cast 172 may be scanned by a measurement system in accordance with conventional techniques. In accordance with at least one embodiment, jawbone cast 172 may be fitted with measurement targets if required by the measurement system.

At step 318, a 3D model may be generated using the measurements taken from impression device 100 at step 312 and/or from jawbone cast 172 at step 316. In accordance with at least one embodiment, where impression device 100 and jawbone cast 172 are both measured and provide conflicting measurement data, the final measurement data may be averaged or determined using an alternative algorithm (e.g. to produce a lowest root mean square discrepancy).

Figure 20:
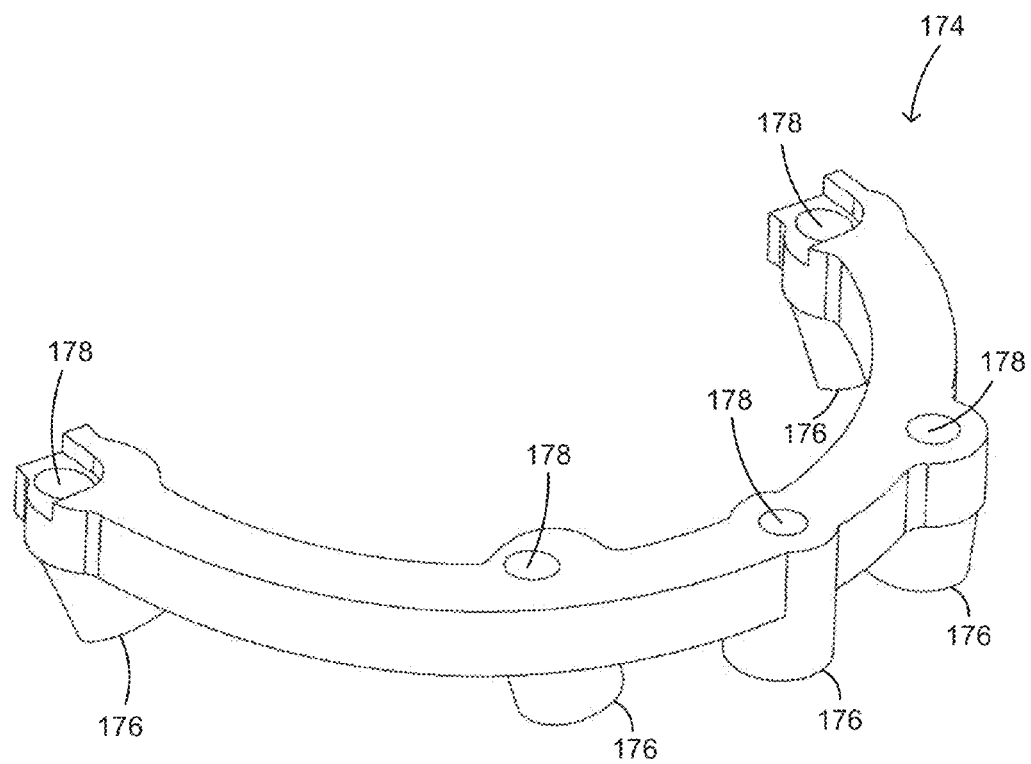
FIG. 20 is a perspective view of a framework in accordance with at least one embodiment.

At step 320, a framework 174 may be manufactured using the 3D model generated at step 318. FIG. 20 shows an example of a framework 174 that may be manufactured according to method 300. In the example shown, framework 174 includes implant interfaces 176 that have been made to couple with the implants 12. As shown, each implant interface 176 includes a through-hole 178 configured to receive a fastener (e.g a screw) for securing framework 174 onto a patient's implants 12.

Figure 21:
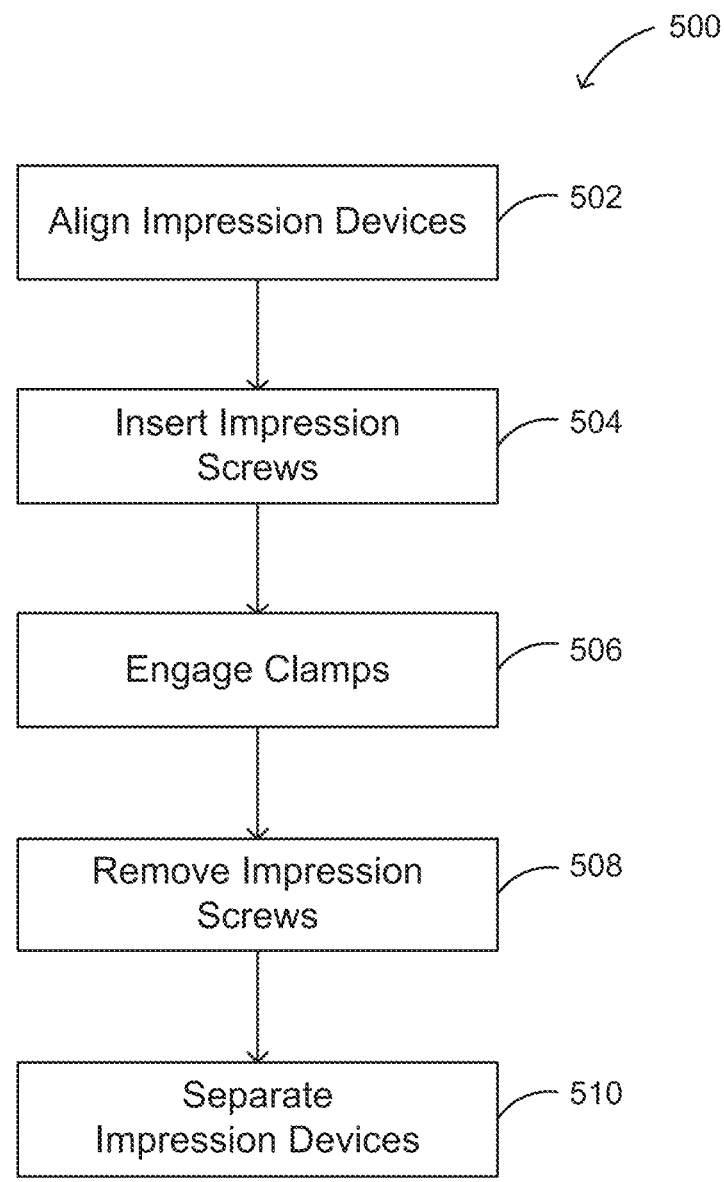
FIG. 21 shows a flowchart illustrating a method for configuring a positive impression device in accordance with at least one embodiment.

At step 324, a positive impression device may be configured. FIG. 21 shows a flowchart illustrating a method 500 for configuring a positive impression device.

Figure 22:
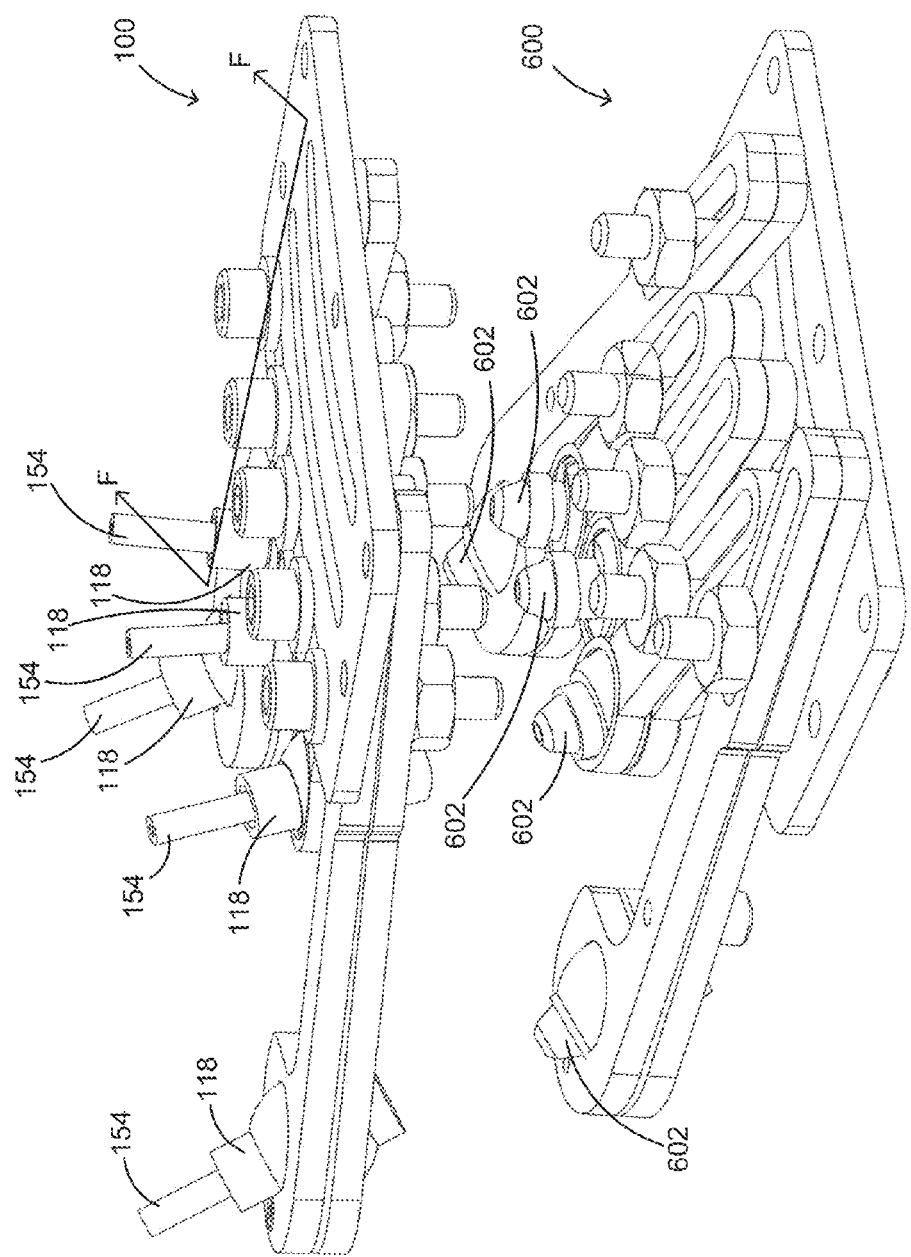
FIG. 22 is a perspective view of the impression device of FIG. 1 and a positive impression device in accordance with at least one embodiment.

At step 502, a positive impression device 600 may be aligned with impression device 100. The location and orientation of copings 118 have been previously locked by the engagement of clamps 126 at 306. FIG. 22 shows an example of a positive impression device 600 positioned below impression device 100. As shown, impression device 600 is similar to impression device 100, except that copings 118 have been replaced by implant analogues 602. Like reference numerals refer to similar elements. Accordingly, implant analogues 602 may have multiple degrees of freedom to permit them to precisely align with copings 118 of impression device 100.

Figure 23:
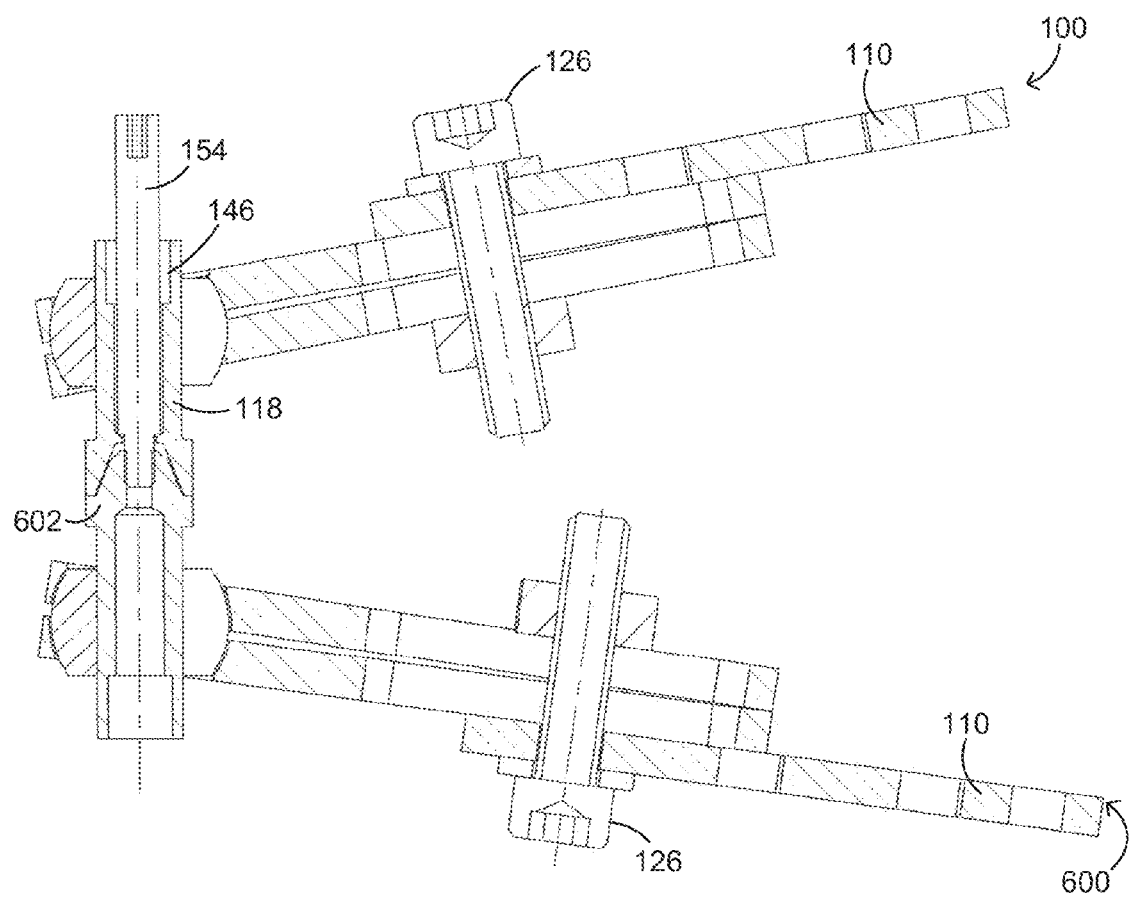
FIG. 23 is a partial cross-sectional view taken along line F-F of FIG. 22 showing the impression device of FIG. 1 secured to the positive impression device of FIG. 22 in accordance with at least one embodiment.

At step 504, an impression screw 154 may be inserted into a through-hole 146 of each coping 118. As shown in FIG. 23, each impression screw 154 secures an implant analogue 602 in mating relationship with a coping 118.

At step 506, clamps 126 of positive impression device 600 may be engaged. This may lock the location and orientation of implant analogues 602 with respect to base 110 of positive impression device 600.

At step 508 the impression screws 154 may be removed from the implant analogues 602 thereby decoupling the positive impression device 600 from the impression device 100. At step 510, the positive impression device 600 may be separated from impression device 100.

Figure 24:
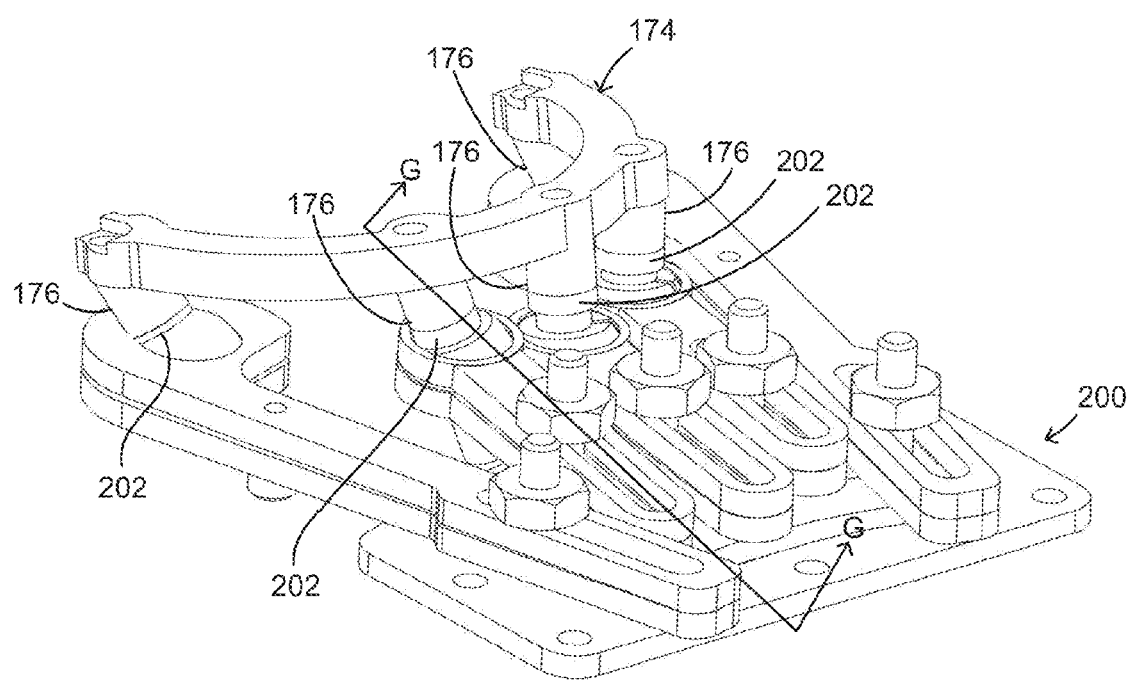
FIG. 24 is a perspective view of the positive impression device of FIG. 22 aligned with the framework of FIG. 20 in accordance with at least one embodiment.

Referring again to FIG. 8, at step 326, framework 174 may be tested using positive impression device 600. FIG. 24 shows an example of a framework 174 having implant interfaces 176 aligned in mating relationship with implant analogues 602 of positive impression device 600.

Figure 25:
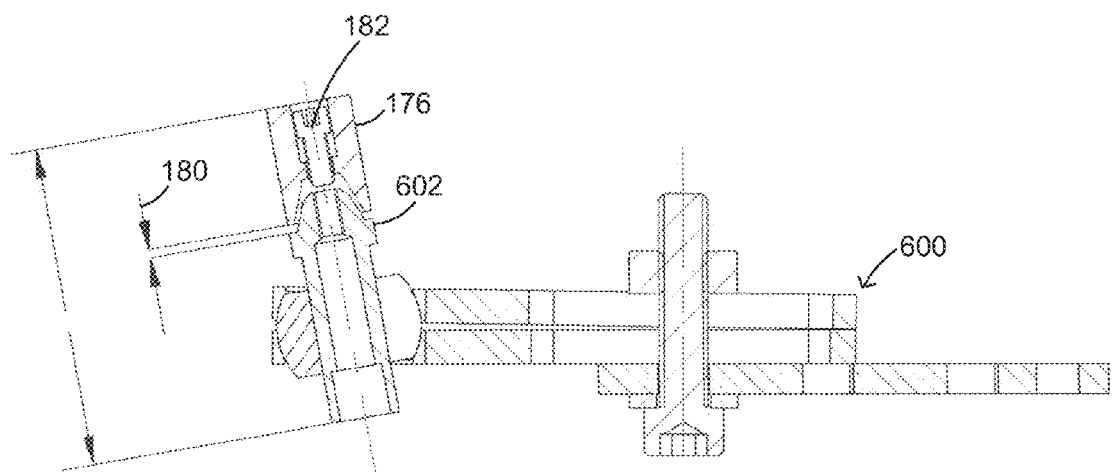
FIG. 25 is a partial cross-sectional view taken along line G-G of FIG. 24 in accordance with at least one embodiment.
Figure 26:
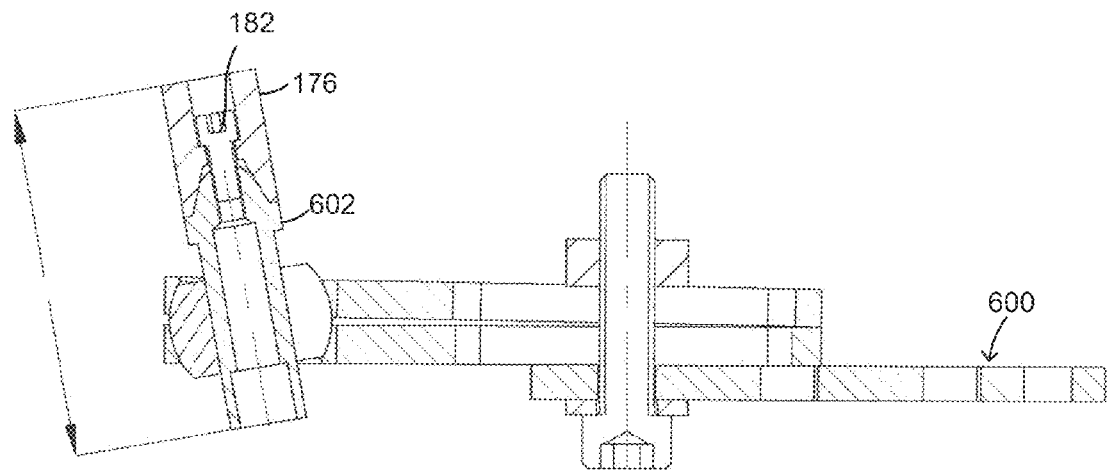

As shown in FIG. 25, after framework 174 is mated with positive impression device 600, a gap 180 between some implant analogues 602 and implant interfaces 176 may occur. A measured gap 180 may represent an alignment error. If gap 180 is too large, then closing the gap 180 by tightening implant screw 182 may deform framework 174 or implant 12. This may introduce undesirable stress onto framework 174 and/or compromise implant 12. FIG. 26 shows framework 174 and positive impression device 600 of FIG. 25 after tightening implant screw 182 to close gap 180.

At 328, it is determined whether the framework 174 requires adjustment or remanufacturing based upon the measured gap(s) 180, if any. If adjustment is required, the framework 174 is adjusted or remanufactured at 320. If not, the method ends at 330.

While particular embodiments have been illustrated and described, it will be apparent to those skilled in the art that various other changes and modifications may be made without departing from the scope of the present application. It is therefore intended to cover in the appended claims all such changes and modifications.

The invention claimed is:

1. An apparatus for measuring a location and orientation of each of a plurality of dental implants, comprising:
    a base; and
    a plurality of extension members protruding from the base, wherein each of the plurality of extension members is movable in relation to the base, each extension member comprising:
        a proximal end connected to the base,
        a distal end, and
        a coping connected to the distal end, wherein the coping is movable in relation to a corresponding extension member, and wherein the coping is adapted to be mechanically locked in a selected location and orientation; and
    a plurality of clamps, wherein each of the plurality of clamps is adapted to lock a corresponding extension member to the base;
    wherein each extension member comprises an elongate upper portion and an elongate lower portion, and
    wherein each of the plurality of clamps is adapted to urge one of the upper and lower portions toward the other of the upper and lower portions of a corresponding extension member.

2. The apparatus of claim 1, wherein each of the plurality of clamps is adapted to lock a corresponding coping in the selected location and orientation.

3. The apparatus of claim 1,
    wherein each coping is at least partially received in a corresponding spherical member, and
    wherein each of the plurality of clamps is adapted to urge the upper and lower portions of the corresponding extension member against an external surface of the corresponding spherical member to lock a location and orientation of the corresponding spherical member with respect to the extension member.

4. The apparatus of claim 3,
    wherein each coping is at least partially received in a through-hole of the corresponding spherical member, wherein the through-hole is defined by an interior surface of the spherical member, and
    wherein each of the plurality of clamps is adapted to urge the upper and lower portions of the corresponding extension member against the external surface of the corresponding spherical member to reduce a diameter of the through-hole of the corresponding spherical member, thereby urging the interior surface of the corresponding spherical member against the corresponding coping, to lock the location and orientation of the coping with respect to the base.

5. The apparatus of claim 1 wherein the coping is connected to the corresponding extension member by a ball joint.

6. The apparatus of claim 1,
wherein the base comprises at least one slot;
wherein each of the plurality of clamps passes through one of the at least one slot; and
wherein each of the plurality of clamps is adapted to lock the corresponding extension member relative to the corresponding slot.

7. The apparatus of claim 1 wherein
each coping defines a through-hole adapted to receive a screw connected to one of the plurality of dental implants.

8. The apparatus of claim 7 wherein
the through-hole of each coping is sized to receive a measurement target detectable by a control measurement device.

9. The apparatus of claim 1 wherein
the location and orientation of each coping is fixed with respect to the corresponding extension member;
each coping is rotatable about the corresponding extension member in at least two orthogonal axes; and
each clamp is adapted to resist rotation of the corresponding coping relative to the corresponding extension member.

10. The apparatus of claim 9 wherein
at least one extension member is positionable along a plane, and
each extension member is rotatable about an axis perpendicular to the plane, the axis being concentric with the corresponding clamp.

11. An apparatus for replicating a location and orientation of each of a plurality of dental implants, comprising:
a base; and
a plurality of extension members protruding from the base, wherein each of the plurality of extension members is movable in relation to the base, each extension member comprising:
a proximal end connected to the base,
a distal end, and
an implant analogue connected to the distal end, wherein the implant analogue is movable in relation to a corresponding extension member, and wherein the implant analogue is adapted to be mechanically locked in a selected location and orientation; and
a plurality of clamps, wherein each of the plurality of clamps is adapted to lock a corresponding extension member to the base;
wherein each extension member comprises an elongate upper portion and an elongate lower portion, and
wherein each of the plurality of clamps is adapted to urge one of the upper and lower portions toward the other of the upper and lower portions of a corresponding extension member.

12. The apparatus of claim 11, wherein each of the plurality of clamps is adapted to lock a corresponding implant analogue in the selected location and orientation.

13. The apparatus of claim 11,
wherein each implant analogue is at least partially received in a corresponding spherical member, and
wherein each of the plurality of clamps is adapted to urge the upper and lower portions of the corresponding extension member against an external surface of the corresponding spherical member to lock a location and orientation of the corresponding spherical member with respect to the extension member.

14. The apparatus of claim 13
wherein each implant analogue is at least partially received in a through-hole of the corresponding spherical member, wherein the through-hole is defined by an interior surface of the spherical member, and
wherein each of the plurality of clamps is adapted to urge the upper and lower portions of the corresponding extension member against the external surface of the corresponding spherical member to reduce a diameter of the through-hole of the corresponding spherical member thereby urging the interior surface of the corresponding spherical member against the corresponding implant analogue, to lock the location and orientation of the implant analogue with respect to the base.

15. The apparatus of claim 11 wherein the implant analogue is connected to the corresponding extension member by a ball joint.

16. The apparatus of claim 11,
wherein the base comprises at least one slot;
wherein each of the plurality of clamps passes through one of the at least one slot; and
wherein each of the plurality of clamps is adapted to lock the corresponding extension member relative to the corresponding slot.

17. The apparatus of claim 11 wherein
the location and orientation of each implant analogue is fixed with respect to the corresponding extension member;
each implant analogue is rotatable about the corresponding extension member in at least two orthogonal axes; and
each clamp is adapted to resist rotation of the corresponding implant analogue relative to the corresponding extension member.

18. The apparatus of claim 11 wherein
at least one extension member is positionable along a plane, and
each extension member is rotatable about an axis perpendicular to the plane, the axis being concentric with the corresponding clamp.

* * * * *